US011402394B2

(12) United States Patent
Chakrabartty et al.

(10) Patent No.: US 11,402,394 B2
(45) Date of Patent: *Aug. 2, 2022

(54) ANTIBODIES TO TTR AND METHODS OF USE

(71) Applicant: University Health Network, Toronto (CA)

(72) Inventors: Avijit Chakrabartty, Vaughan (CA); Rishi Rakhit, Menlo Park, CA (US); Anita Antoinette Bugyei-Twum, Scarborough (CA)

(73) Assignee: University Health Network, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/198,965

(22) Filed: Nov. 23, 2018

(65) Prior Publication Data
US 2019/0195896 A1 Jun. 27, 2019

Related U.S. Application Data

(60) Division of application No. 15/373,657, filed on Dec. 9, 2016, now abandoned, which is a continuation of
(Continued)

(51) Int. Cl.
*C07K 16/18* (2006.01)
*A61K 51/10* (2006.01)
*C07K 16/46* (2006.01)
*G01N 33/78* (2006.01)
*C07K 16/26* (2006.01)
(Continued)

(52) U.S. Cl.
CPC ............ *G01N 33/78* (2013.01); *C07K 14/47* (2013.01); *C07K 14/575* (2013.01); *C07K 16/18* (2013.01); *C07K 16/26* (2013.01);

*G01N 33/74* (2013.01); *C07K 2317/34* (2013.01); *C07K 2317/76* (2013.01); *G01N 2800/046* (2013.01);
(Continued)

(58) Field of Classification Search
None
See application file for complete search history.

(56) References Cited

U.S. PATENT DOCUMENTS 9,534,048 B2   1/2017   Chakrabartty et al.
2003/0232758 A1*  12/2003   St. George-Hyslop ..................... C07K 14/4711
514/17.7

(Continued)

FOREIGN PATENT DOCUMENTS

WO   2010/030203 A1   3/2010

OTHER PUBLICATIONS

Goldsteins, Gundars et al. Exposure of cryptic epitopes on transthyretin only in amyloid and in amyloidogenic mutants. Proc. Natl. Acad. Sci. USA, vol. 96, pp. 3108-3113, Mar. 1999.
(Continued)

*Primary Examiner* — Aurora M Fontainhas
(74) *Attorney, Agent, or Firm* — Carmela De Luca; Bereskin & Parr LLP

(57) ABSTRACT

The disclosure pertains to antibodies and binding fragments thereof that specifically binds all or part of EHAEVVFTA. Also provided are isolated peptides, isolated nucleic acids, immunogens, compositions, immunoassays and kits and method of using said reagents to detect misfolded TTR.

20 Claims, 4 Drawing Sheets
Specification includes a Sequence Listing.

Related U.S. Application Data application No. 13/974,761, filed on Aug. 23, 2013, now Pat. No. 9,534,048.

(60) Provisional application No. 61/692,916, filed on Aug. 24, 2012.

(51) Int. Cl.
  *G01N 33/74* (2006.01)
  *C07K 14/575* (2006.01)
  *C07K 14/47* (2006.01)

(52) U.S. Cl.
  CPC ... *G01N 2800/28* (2013.01); *G01N 2800/325* (2013.01); *G01N 2800/7047* (2013.01)

(56) References Cited

U.S. PATENT DOCUMENTS

2005/0266467 A1    12/2005   Roy
2006/0057701 A1*    3/2006   Rosenthal .............. A61K 39/00
                                                      435/252.3

OTHER PUBLICATIONS

Almeida Palha, Joana et al. Antibody recognition of amyloidogenic transthyretin variants in serum of patients with familial amyloidotic polyneuropathy. J. Mol. Med. 2001, 78:703-707.

Bergstrom, Joakim et al. Surface exposed epitopes and structural heterogeneity of in vivo formed transthyretin amyloid fibrils. Biochemical and Biophysical Research Communications, 348 (2006) 532-539.

Bugyei-Twum, Antoinette. Inhibition of Transthyretin Fibrillogenesis Using a Conformation Specific Antibody. Thesis archived on Mar. 21, 2012.

Adekar SP, Klyubin I, Macy S, Rowan MJ, Solomon A, Dessain SK, O'Nuallain B. Inherent anti-amyloidogenic activity of human immunoglobulin gamma heavy chains. J Biol Chem. Jan. 8, 2010;285(2):1066-74. doi: 10.1074/jbc.M109.044321. PubMed PMID: 19889627; PubMed Central PMCID: PMC2801233.

Cardoso I, Goldsbury CS, Müller SA, Olivieri V, Wirtz S, Damas AM, Aebi U, Saraiva MJ. Transthyretin fibrillogenesis entails the assembly of monomers: a molecular model for in vitro assembled transthyretin amyloid-like fibrils. J Mol Biol. Apr. 12, 2002;317(5):683-95. PubMed PMID: 11955017.

Chen JJ, Genereux JC, Suh EH, Vartabedian VF, Rius B, Qu S, Dendle MT, Kelly JW, Wiseman RL. Endoplasmic Reticulum Proteostasis Influences the Oligomeric State of an Amyloidogenic Protein Secreted from Mammalian Cells. Cell Chem Biol. Oct. 20, 2016;23(10):1282-1293. doi: 10.1016/j.chembiol.2016.09.001. PubMed PMID: 27720586 PubMed Central PMCID: PMC5108364.

Galant NJ, Bugyei-Twum A, Rakhit R, Walsh P, Sharpe S, Arslan PE, Westermark P, Higaki JN, Torres R, Tapia J, Chakrabartty A. Substoichiometric inhibition of transthyretin misfolding by immune-targeting sparsely populated misfolding intermediates: a potential diagnostic and therapeutic for TTR amyloidoses. Sci Rep. Apr. 28, 2016;6:25080. doi: 10.1038/srep25080. PubMed PMID: 27122057; PubMed Central PMCID: PMC4848561.

Higaki JN, Chakrabartty A, Galant NJ, Hadley KC, Hammerson B, Nijjar T, Torres R, Tapia JR, Salmans J, Barbour R, Tam SJ, Flanagan K, Zago W, Kinney GG. Novel conformation-specific monoclonal antibodies against amyloidogenic forms of transthyretin. Amyloid. Jun. 2016;23(2):86-97. doi: 10.3109/13506129.2016.1148025. PubMed PMID 26981744; PubMed Central PMCID: PMC4898150.

Jiang X, Smith CS, Petrassi HM, Hammarström P, White JT, Sacchettini JC, Kelly JW. An engineered transthyretin monomer that is nonamyloidogenic, unless it is partially denatured. Biochemistry. Sep. 25, 2001;40(38):11442-52. PubMed PMID: 11560492.

Johnson SM, Connelly S, Fearns C, Powers ET, Kelly JW. The transthyretin amyloidoses: from delineating the molecular mechanism of aggregation linked to pathology to a regulatory-agency-approved drug. J Mol Biol. Aug. 10, 2012;421(2-3):185-203. doi: 10.1016/j.jmb.2011.12.060. Review. PubMed PMID: 22244854; PubMed Central PMCID: PMC3350832.

Lai Z, Colón W, Kelly JW. The acid-mediated denaturation pathway of transthyretin yields a conformational intermediate that can self-assemble into amyloid. Biochemistry. May 21, 1996;35(20):6470-82. PubMed PMID 8639594.

Lashuel HA, Lai Z, Kelly JW. Characterization of the transthyretin acid denaturation pathways by analytical ultracentrifugation: implications for wild-type, V30M, and L55P amyloid fibril formation. Biochemistry. Dec. 22, 1998;37(51):17851-64. PubMed PMID: 9922152.

Levites Y, O'Nuallain B, Puligedda RD, et al. A human monoclonal IgG that binds aβ assemblies and diverse amyloids exhibits anti-amyloid activities in vitro and in vivo. J Neurosci. Apr. 22, 2015;35(16):6265-76. doi: 10.1523/JNEUROSCI.5109-14.2015. PubMed PMID: 25904780; PubMed Central PMCID: PMC4405548.

McCutchen SL, Lai Z, Miroy GJ, Kelly JW, Colón W. Comparison of lethal and nonlethal transthyretin variants and their relationship to amyloid disease. Biochemistry. Oct. 17, 1995;34(41):13527-36. PubMed PMID: 7577941.

Miroy GJ, Lai Z, Lashuel HA, Peterson SA, Strang C, Kelly JW. Inhibiting transthyretin amyloid fibril formation via protein stabilization. Proc Natl Acad Sci USA. Dec. 24, 1996;93(26):15051-6. PubMed PMID: 8986762; PubMed Central PMCID: PMC26354.

O'Nuallain B, Allen A, Kennel SJ, Weiss DT, Solomon A, Wall JS. Localization of a conformational epitope common to non-native and fibrillar immunoglobulin light chains. Biochemistry. Feb. 6, 2007;46(5):1240-7. PubMed PMID: 17260953; PubMed Central PMCID: PMC1832162.

O'Nuallain B, Wetzel R. Conformational Abs recognizing a generic amyloid fibril epitope. Proc Natl Acad Sci U S A. Feb. 5, 2002;99(3):1485-90. PubMed PMID: 11818542; PubMed Central PMCID: PMC122217.

O'Nuallain B, Williams AD, McWilliams-Koeppen HP, Acero L, Weber A, Ehrlich H, Schwarz HP, Solomon A. Anti-amyloidogenic activity of IgGs contained in normal plasma. J Clin Immunol. May 2010;30 Suppl 1:S37-42. doi: 10.1007/s10875-010-9413-6. PubMed PMID: 20405179; PubMed Central PMCID: PMC2883095.

Phay M, Blinder V, Macy S, Greene MJ, Wooliver DC, Liu W, Planas A, Walsh DM, Connors LH, Primmer SR, Planque SA, Paul S, O'Nuallain B. Transthyretin aggregate-specific antibodies recognize cryptic epitopes on patient-derived amyloid fibrils. Rejuvenation Res. Apr. 2014;17(2):97-104. doi: 10.1089/rej.2013.1524. PubMed PMID: 24164623.

Phay M, Welzel AT, Williams AD, McWilliams-Koeppen HP, Blinder V, O'Malley TT, Solomon A, Walsh DM, O'Nuallain B. IgG Conformer's Binding to Amyloidogenic Aggregates. PLoS One. Sep. 14, 2015;10(9):e0137344. doi: 10.1371/journal.pone.0137344. PubMed PMID: 26367058; PubMed Central PMCID: PMC4569075.

Planque SA, Nishiyama Y, Hara M, Sonoda S, Murphy SK, Watanabe K, Mitsuda Y, Brown EL, Massey RJ, Primmer SR, O'Nuallain B, Paul S. Physiological IgM class catalytic antibodies selective for transthyretin amyloid. J Biol Chem. May 9, 2014;289(19):13243-58. doi:10.1074/jbc.M114.557231. PubMed PMID: 24648510; PubMed Central PMCID: PMC4036335.

Planque SA, Nishiyama Y, Sonoda S, Lin Y, Taguchi H, Hara M, Kolodziej S, Mitsuda Y, Gonzalez V, Sait HB, Fukuchi K, Massey RJ, Friedland RP, O'Nuallain B, Sigurdsson EM, Paul S. Specific amyloid β clearance by a catalytic antibody construct. J Biol Chem. Apr. 17, 2015;290(16):10229-41. doi: 10.1074/jbc.M115.641738. PubMed PMID: 25724648; PubMed Central PMCID: PMC4400338.

Quintas A, Vaz DC, Cardoso I, Saraiva MJ, Brito RM. Tetramer dissociation and monomer partial unfolding precedes protofibril formation in amyloidogenic transthyretin variants. J Biol Chem. Jul. 20, 2001;276(29):27207-13. PubMed PMID: 11306576.

Redondo C, Damas AM, Olofsson A, Lundgren E, Saraiva MJ. Search for intermediate structures in transthyretin fibrillogenesis: soluble tetrameric Tyr78Phe TTR expresses a specific epitope

(56) References Cited

OTHER PUBLICATIONS present only in amyloid fibrils. J Mol Biol. Dec. 1, 2000;304(3):461-70. PubMed PMID: 11090287.

Su Y, Jono H, Torikai M, Hosoi A, Soejima K, Guo J, Tasaki M, Misumi Y, Ueda M, Shinriki S, Shono M, Obayashi K, Nakashima T, Sugawara K, Ando Y. Antibody therapy for familial amyloidotic polyneuropathy. Amyloid 2012;19:45¬6.

Hosoi A, Su Y, Torikai M, Jono H, Ishikawa D, Soejima K, Higuchi H, Guo J, Ueda M, Suenaga G, Motokawa H, Ikeda T, Senju S, Nakashima T, Ando Y. Novel Antibody for the Treatment of Transthyretin Amyloidosis. J Biol Chem. Nov. 25, 2016;291(48):25096-25105.

Gustavsson et al., Mechanisms of Transthyretin Amyloidogenesis Antigenic Mapping of Transthyretin Purified from Plasma and Amyloid Fibrills and within in Situ Tissue Localizations. American Journal of Pathology, vol. 144, No. 6, Jun. 1994, 1301-1311.

Edwards et al. The Remarkable Flexibility of the Human Antibody Repertoire; Isolation of Over One Thousand Different Antibodies to a Single Protein, BLyS. J. Mol. Biol. (2003) 334, 103-118.

Sharma S. et al. Identification of Autoantibodies against Transthyretin for the Screening and Diagnosis of Rheumatoid Arthritis. PLoS ONE 9(4): e93905, 2014.

Reichert et al. Monoclonal antibody successes in the clinic. Nature Biotechnology, 1073-1078, 2005.

Walsh, Patrick et al. Core Structure of Amyloid Fibrils Formed by Residues 106-126 of the Human Prion Protein. Structure 17, 417-426, Mar. 2009.

Kelly, Jeffery W. Amyloid fibril formation and protein misassembly: a structural quest for insights into amyloid and prion diseases. Structure, 1997, vol. 5, No. 5, 595-600.

Liu, Kai et al. A glimpse of a possible amyloidogenic intermediate of transthyretin. Natural Structural Biology, vol. 7, No. 9, 2000, 754-757.

Come, Jon H. et al. A kinetic model for amyloid formation in the prion diseases: Importance of seeding. Proc. Natl. Acad. Sci. vol. 90, pp. 5959-5963, 1993.

Jiang, Xing et al. The V122I cardiomyopathy variant of transthyretin increases the velocity of rate-limiting tetramer dissociation, resulting in accelerated amyloidosis. PNAS, Dec. 18, 2001, vol. 98, No. 26, 14943-14948.

\* cited by examiner

SEQUENCE LISTING

```
<160> NUMBER OF SEQ ID NOS: 3

<210> SEQ ID NO 1
<211> LENGTH: 9
<212> TYPE: PRT
<213> ORGANISM: Homo Sapien

<400> SEQUENCE: 1

Glu His Ala Glu Val Val Phe Thr Ala
1               5

<210> SEQ ID NO 2
<211> LENGTH: 15
<212> TYPE: PRT
<213> ORGANISM: Artificial
<220> FEATURE:
<223> OTHER INFORMATION: Synthetic Construct

<400> SEQUENCE: 2

Gly Gly Glu His Ala Glu Val Val Phe Thr Ala Gly Gly Lys Gly
1               5                   10                  15

<210> SEQ ID NO 3
<211> LENGTH: 9
<212> TYPE: PRT
```

```
<213> ORGANISM: Homo Sapien
<220> FEATURE:
<221> NAME/KEY: misc_feature
<222> LOCATION: (1)..(1)
<223> OTHER INFORMATION: Xaa can be either of Gln or Lys
<220> FEATURE:
<221> NAME/KEY: misc_feature
<222> LOCATION: (3)..(3)
<223> OTHER INFORMATION: Xaa can be either of Ala or Ser
<220> FEATURE:
<221> NAME/KEY: misc_feature
<222> LOCATION: (9)..(9)
<223> OTHER INFORMATION: Xaa can be either of Gly or Ser

<400> SEQUENCE: 3

Xaa His Xaa Glu Val Val Phe Thr Xaa
1               5
```

ANTIBODIES TO TTR AND METHODS OF USE

This application is a divisional of U.S. application Ser. No. 15/373,657, filed on Dec. 9, 2016, which is a continuation of U.S. application Ser. No. 13/974,761, filed on Aug. 23, 2013, which claims the benefit of U.S. Provisional Application No. 61/692,916 filed on Aug. 24, 2012, each of which are incorporated herein in their entirety by reference.

SEQUENCE LISTING

A computer readable form of the Sequence Listing "P42451 US02SL.txt" (1030 bytes), submitted via EFS-WEB and created on Aug. 22, 2013, is herein incorporated by reference.

FIELD

The disclosure relates to antibodies for detecting misfolded proteins and specifically to antibodies for detecting misfolded transthyretin (TTR) intermediates.

INTRODUCTION

Protein misfolding diseases involve the conversion of native proteins into abnormal conformations, which can result in aggregation. The misfolding pathway can in many cases be described by a nucleation and growth model. The native protein must first overcome an energetic barrier to populate transient high-energy intermediates. Conversion of these intermediates to aggregates is an energetically favorable process, and pre-formed aggregates can 'seed' the conversion of other native proteins into the misfolded form. There are several conceptual strategies available for detection of the various molecular species formed along the protein misfolding pathway (FIG. 1).

Under steady-state conditions the native state and fibril state are the most stable and highly populated, but the oligomeric intermediates thought to be responsible for toxicity are sparsely populated.

Several groups have identified epitopes in TTR. Bergstrom J et al. investigated the structure of in vivo formed transthyretin (TTR) amyloid deposits by using antisera raised against short linear sequences of the TTR molecule. In immunohistochemistry, antisera anti-TTR41-50 and anti-TTR115-124-a reacted specifically with both wildtype ATTR and ATTR V30M material, whereas only anti-TTR41-50 recognized ATTR Y114C material. Similar results were obtained by ELISA analysis of ATTR V30M and ATTR Y114C vitreous amyloid, where the anti-TTR115-124-a antiserum failed to react with ATTR Y114C material. Moreover, neither of the antisera recognized natively structured TTR present in pancreatic alpha cells.

Goldsteins G et al generated two monoclonal antibodies against a mutant. Each displayed affinity to ex vivo TTR and TTR mutants with amyloidogenic folding but not to wild-type TTR or mutants exhibiting the wild-type fold. Two cryptic epitopes were mapped to a domain of TTR (residues 39-44 and 56-61) where most mutations associated with amyloidosis occur. Goldsteins et al proposed that these regions become exposed during the initial phase of amyloid formation, opening up new surfaces necessary for autoaggregation of TTR monomers.

Palha JA et al developed an ELISA using monoclonal antibody, MAb 39-44 and identified three different TTR mutations in Portuguese patients with neuropathy of unknown cause, later shown to have amyloid tissue deposition.

SUMMARY

An aspect includes an antibody or binding fragment thereof that specifically binds all or part of EHAEVVFTA (SEQ ID NO:1) and/or an antibody or binding fragment thereof that specifically binds all or part of $X_1HX_2EVVFTX_3$ where $X_1$ can be Q or K, $X_2$ can be A or S, and $X_3$ can be G or S (SEQ ID NO:3).

In an embodiment the antibody is isolated.

In an embodiment, the part specifically bound comprises at least 4, at least 5 or more contiguous amino acids of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, the antibody or binding fragment thereof specifically binds a non-native forms such as misfolded and/or monomeric forms of TTR. In yet another embodiment, the antibody or binding fragment thereof specifically binds monomeric TTR. In an embodiment, the antibody or binding fragment thereof specifically binds tetrameric TTR. In another embodiment, the antibody or binding fragment thereof specifically binds TTR fibrils.

In another embodiment, the antibody or binding fragment thereof is capable of disrupting or reducing TTR fibril formation when non-native forms such as misfolded forms of TTR and/or monomeric TTR (folded or misfolded) in solution is contacted with the antibody or binding fragment.

In another embodiment, a substochiometric amount of antibody or binding fragment thereof compared to TTR monomer and/or tetramer is required to disrupt or reduce TTR fibril formation.

In another embodiment, the antibody is a monoclonal or polyclonal antibody.

In yet another embodiment, the antibody is chimeric or humanized antibody.

In a further embodiment, the antibody fragment is a Fab, Fab', F(ab')$_2$, scFv, dsFv, ds-scFv, dimer, minibody, diabody, or multimer thereof or a bispecific antibody fragment.

In another embodiment, the antibody is purified optionally affinity purified.

Also provided in another embodiment, is an isolated peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3), the part comprising at least 4 or at least 5 or more contiguous amino acids.

In an embodiment, the isolated peptide further comprises one or more amino acid linkers conjugated to one or more of the peptide N and/or C termini.

In another embodiment, the amino acid linkers include one or more G or K or S residues and for example the amino acid linker or linkers each independently comprise GG or GGKG.

In an embodiment, the 5' linker is GG. In an embodiment, the 3' linker is GGKG.

In another embodiment, the isolated peptide comprising linkers comprises all or part of GGEHAEVVFTAGGKG (SEQ ID NO:2).

In an embodiment, the isolated peptide is synthesized using Fmoc protected amino acids.

In another embodiment, the isolated peptide is specifically bound by an antibody described herein.

A further aspect comprises an isolated peptide comprising all or part of: i) EHAEVVFTA (SEQ ID NO:1) and/or ii) $X_1HX_2EVVFTX_3$ where $X_1$ can be Q or K, $X_2$ can be A or S, and $X_3$ can be G or S (SEQ ID NO:3); and a tag.

A further aspect is an isolated nucleic acid encoding an isolated peptide described herein.

Also included in another aspect is an immunogen comprising a peptide, the peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In an embodiment, the immunogen comprises an immunogenicity enhancing molecule conjugated to the peptide.

In an embodiment, the immunogenicity enhancing molecule is keyhole limpet hemocyanin, albumin, or a multiple antigenic peptide dendrimer.

In another embodiment, the immunogen comprises a peptide with one or more linkers.

In another embodiment, the one or more linkers is/are amino acid linkers conjugated to one or more of the peptide N and/or C termini.

In another embodiment, each linker comprises one or more amino acid residues, up to for example 2, 3, 4, or 5 amino acids, wherein the amino acid residues selected from glycine and/or lysine.

In yet another embodiment, the linker or linkers each selected independently comprise GG or GGKG.

In a further embodiment, the peptide linker conjugate sequence is GGEHAEVVFTAGGKG (SEQ ID NO:2).

In another embodiment, the immunogen comprises multiple peptides each peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3) and optionally one or more linkers, wherein the multiple peptides are synthesized as a multiple antigenic peptide (MAP).

In another embodiment, the immunogen is capable of eliciting production of an antibody that specifically binds all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, the immunogen is used to producing an antibody that specifically binds all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, wherein the antibody produced specifically binds a non-native form of TTR such as misfolded and/or monomeric TTR.

A further aspect includes a composition comprising an antibody, isolated peptide, isolated nucleic acid or an immunogen described herein and a suitable carrier.

In an embodiment, composition comprises the isolated peptide, or immunogen and further comprises an adjuvant.

In another embodiment, the adjuvant is selected from Freund's complete and incomplete adjuvant.

A further aspect includes an immunoassay comprising an antibody described herein.

In an embodiment, the immunoassay is an ELISA.

Also provided is a kit, comprising an antibody, isolated peptide, isolated nucleic acid, immunogen, composition and/or immunoassay described herein, and a vessel such as a vial for housing the antibody, isolated peptide, isolated nucleic acid, immunogen and/or composition.

In another embodiment, the kit further comprises instructions for use in a method described herein.

A further aspect includes a method for preparing an antibody, the method comprising immunizing a non-human subject with a peptide, an immunogen or composition described herein.

In an embodiment, the method further comprises isolating an antibody that specifically binds EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, the method further comprises forming antibody-producing hybridomas.

Another aspect includes a method of detecting a non-native forms of TTR such as misfolded TTR conformations and/or monomeric TTR in a test sample, the method comprising contacting the test sample with an antibody or binding fragment thereof described herein under conditions suitable to form a specific antibody antigen complex between the antibody and TTR; determining if a specific antibody TTR complex is formed thereby detecting misfolded TTR and/or monomeric TTR in the test sample.

In an embodiment the method is for detecting a misfolded TTR conformation in a test sample, the method comprising contacting the test sample with an antibody or binding fragment thereof described under conditions suitable to form a specific antibody antigen complex between the antibody and TTR; determining if a specific antibody TTR complex is formed thereby detecting misfolded TTR in the test sample.

In another embodiment, the method is for detecting monomeric TTR in a test sample, the method comprising contacting the test sample with an antibody or binding fragment thereof described herein under conditions suitable to form a specific antibody TTR complex between the antibody and TTR; determining if a specific antibody TTR complex is formed thereby detecting monomeric TTR in the test sample.

In an embodiment, the misfolded TTR is comprised in TTR fibrils.

In another embodiment, the determining comprises measuring the amount of the antibody-antigen complex in the test sample and comparing the amount of antibody-antigen complex in the test sample to a control, wherein a difference in the amount of antibody-antigen complex in the test sample as compared to the control is indicative that misfolded TTR is detected in the test sample.

In another embodiment, the method is for detecting misfolded TTR and/or monomeric TTR in a subject suspected and/or known to have an amyloid deposition disease.

In an embodiment, the amyloid deposition diseases is a TTR amyloid deposition disease.

Another aspect includes a method of diagnosing a subject with a TTR amyloid deposition disease, the method comprising contacting a test sample obtained from the subject with an antibody or binding fragment thereof described herein under conditions suitable to form a specific antibody antigen complex between the antibody and TTR; determining if a specific antibody TTR complex is formed; and identifying the subject as having or having an increased risk of developing a TTR amyloid deposition disease when specific antibody TTR binding is detected.

In an embodiment, the amyloid deposition disease is selected from an embodiment, the amyloid TTR amyloidosis disease is selected from systemic senile amyloidosis, familial amyloid polyneuropathy, and familial amyloid cardiomyopathy.

In another embodiment, the test sample is a biological sample obtained from a subject.

In another embodiment, the sample comprises blood, serum, plasma, and/or solid tissue.

Also provided is a method of inhibiting TTR fibril formation, the method comprising contacting an antibody or fragment disclosed herein with a sample comprising misfolded TTR and/or monomeric TTR under fibril formation conditions, wherein the antibody specifically binds the misfolded and/or monomeric TTR and inhibits fibril formation.

In an embodiment, the antibody or binding fragment thereof is contracted with misfolded TTR or monomeric TTR during the lag phase of fibril formation.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 2A is a surface representation of human TTR (gray) in its native tetrameric state, with buried epitope in black. FIG. 2B is a surface representation of monomeric TTR (gray), with the exposed epitope highlighted in black. Structures were generated using PDB ID 1DVQ in Deep View (Swiss-PBD Viewer 3.7)

FIG. 3A is a competition ELISA using the misTTR antibody (filled circles) or a commercially available anti-TTR antibody (unfilled circles). Binding selectivity of the misTTR antibody was determined by measuring antibody binding to GdnHCl unfolded TTR coated wells in the presence of increasing concentrations of folded tetrameric TTR in solution. The misTTR antibody preferentially binds GdnHCl-unfolded TTR on the ELISA plate whereas the commercially available antibody readily binds folded tetrameric TTR. FIG. 3B is a competition ELISA with the misTTR antibody, which selectively binds monomeric TTR in the presence of GdnHCl-unfolded TTR immobilized on the ELISA plate.

FIG. 4A is a representative TEM image of amyloid fibrils produced from 1 mg/mL TTR. FIG. 4B is a competition ELISA with the misTTR antibody, which selectively binds TTR amyloid fibrils in the presence of GdnHCl-unfolded TTR. FIG. 4C is a dot blot analysis of native TTR, TTR fibrils, and lysozyme. 250 ng of each protein was spotted onto membrane.

FIG. 5A is a timecourse of TTR fibril formation in the presence (filled squares circles) and absence (filled circles) of the misTTR antibody (67 nM), monitored by ThT fluorescence. Dashed lines are added as guides for the eyes. FIG. 5B is a dose-dependent inhibition of TTR fibril formation using substoichiometric amounts of the misTTR antibody (filled circles), as assessed by ThT. Unfilled circles depict the effect of the commercial anti-TTR antibody on fibril formation. For FIGS. 5A and 5B, ThT fluorescence emission peaks were integrated from 475 nm-495 nm and plotted against time or antibody concentration respectively.

DETAILED DESCRIPTION OF THE DISCLOSURE

I. Definitions

Figure 1:
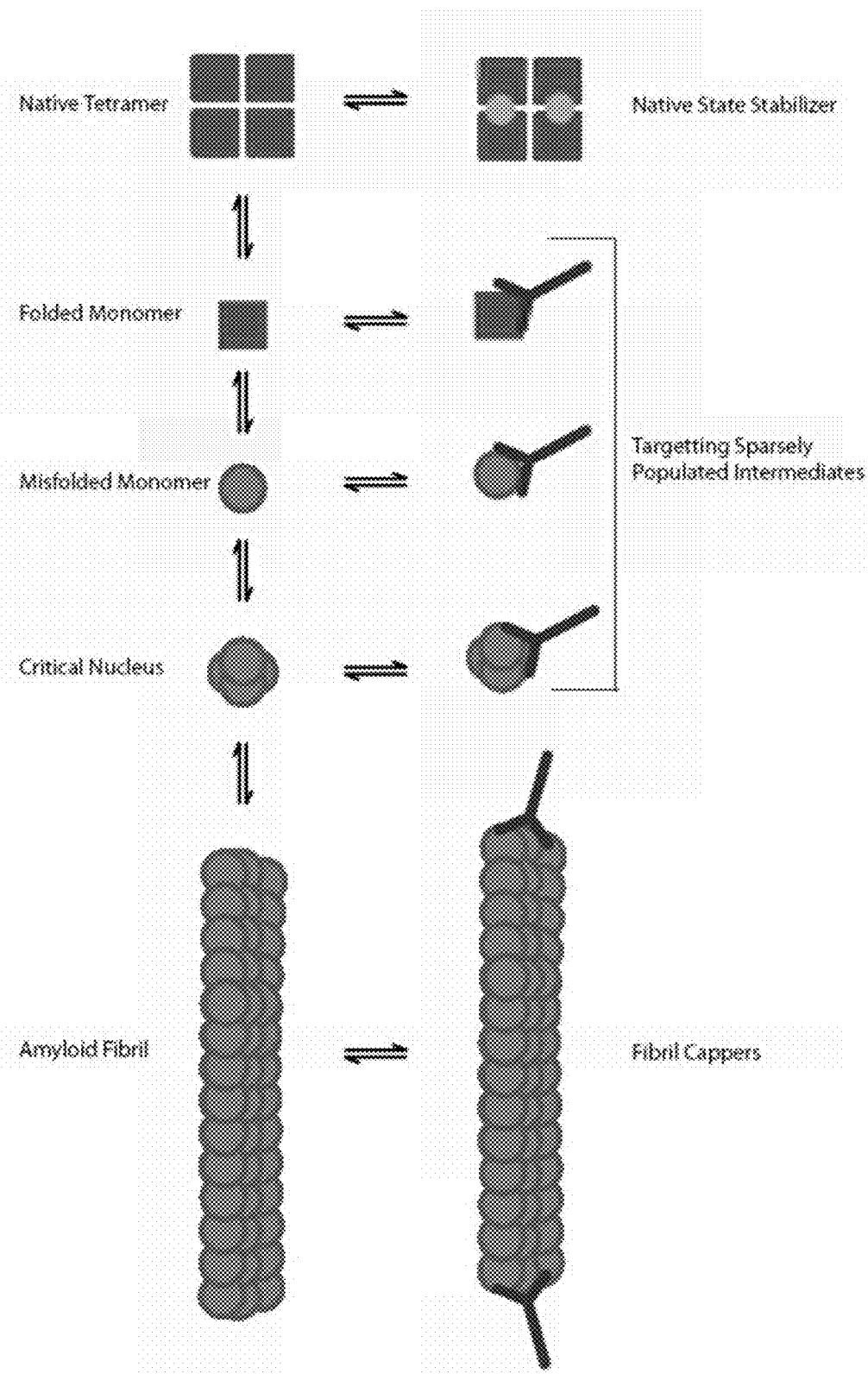
FIG. 1: A schematic diagram displaying the misfolding pathway of TTR and potential sites for interaction with binding molecules.

The term "transthyretin" or "TTR" as used herein means all naturally occurring and TTR polypeptides and polynucleotides including but not limited to mammalian such as human TTR, including those having sequences disclosed in Accession:P02766.1, Accession:AAB35639.1, Accession: AAB35640.1, Accession:ABI63351.1), the sequences of which are each herein incorporated by reference. TTR is a serum and cerebrospinal fluid protein that is synthesized mainly by the liver and was initially referred to as prealbumin and thyroxine binding prealbumin. The name transthyretin was put forth by the Nomenclature Committee of the International Union of Biochemistry (1981) to reflect the molecule's dual function as a transporter of thyroxine and retinol-binding protein In the central nervous system, transthyretin is synthesized de novo by the choroid plexus, a secretory structure located in the ventricles of the brain (Herbert, Wilcox et al. 1986). There, it acts as the primary transport protein for L-thyroxine, transporting up to 80% of the hormone in cerebrospinal fluid (Hagen and Elliott 1973).

The term a "TTR amyloid deposition diseases" or "TTR amyloidoses" as used herein diseases and disorders comprising pathogenic misfolded TTR (e.g. which can result from mutations in TTR as well as non-mutated misfolded TTR) resulting in highly stable, fibrillar aggregates called amyloid, implicated in a number of disorders, including senile systemic amyloidosis, a late onset disease in which wild-type transthyretin deposits primarily in the heart, and the familial amyloid polyneuropathies and cardiomyopathies, wherein point mutations in the gene encoding transthyretin result in the deposition of protein aggregates in the peripheral nerves and heart, respectively. Transthyretin-related familial amyloid polyneuropathies and cardiomyopathies usually have an earlier age of onset than that of the senile form of the disease, occurring as early as the second decade of life. This early age of disease onset is presumably due to the decreased stability of variant transthyretin with respect to the wild-type protein. To date, over 100 mutations in the gene encoding transthyretin have been implicated in the autosomal dominant disorders familial amyloid polyneuropathy and familial amyloid cardiomyopathy (Benson 1989; Damas and Saraiva 2000; Saraiva 2001). These amyloid causing mutations are distributed throughout the entire molecule of transthyretin. A few of these mutations (V30M, L55P, and V122I), however, have been shown to influence the thermodynamic stability of transthyretin, a property which correlates well with disease severity (McCutchen, Colon et al. 1993; McCutchen, Lai et al. 1995; Bonifacio, Sakaki et al. 1996; Quintas, Saraiva et al. 1997; Lashuel, Lai et al. 1998; Shnyrov, Villar et al. 2000; Jiang, Buxbaum et al. 2001; Hammarstrom, Jiang et al. 2002). For instance, mutations known to severely destabilize the native fold of transthyretin, such as the L55P mutation, can display an aggressive pathology with disease onset occurring as early as the second decade of life.

The term "antibody" as used herein is intended to include monoclonal antibodies including chimeric and humanized monoclonal antibodies, polyclonal antibodies, humanized antibodies, human antibodies, and chimeric antibodies. The antibody may be from recombinant sources and/or produced in transgenic animals.

The term "antibody fragment" as used herein is intended to include Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques. The antibodies are optionally in any useful isotype, including IgM which in one embodiment is used for diagnostic applications and IgG, such as IgG1, IgG2, IgG3 and IgG4 which in one embodiment is used for therapeutic applications.

"Isolated antibody" refers to antibody produced in vitro or in vivo that has been removed from the source that produced the antibody, for example, an animal, hybridoma or other cell line (such as recombinant cells that produce antibody). The isolated antibody is optionally "purified", which means at least: 80%, 85%, 90%, 95%, 98% or 99% purity and optionally pharmaceutical grade purity.

"Endogenous antibody" refers to antibody produced by a subject, such as a mammal (eg. human), as part of an immune response to an immunogen in the subject.

"Exogenous antibody" refers to an antibody that is non-self or foreign to a subject, such as a mammal (eg. human). The term "exogenous antibody" encompasses isolated antibody as well as isolated and purified antibody.

The term "humanized antibody" as used herein means that the antibody or fragment comprises human conserved framework regions (alternatively referred to as constant regions) and the hypervariable regions (alternatively referred to as the antigen binding domain) are of non-human origin. For example, the hypervariable region may be from a mouse, rat or other species. The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (eg. Scotgen Limited, 2 Holly Road, Twickenham, Middlesex, Great Britain.)

The term "human antibodies" as used herein refers to antibodies that are, or correspond to, antibodies that are produced endogenously in a human subject, however, human antibodies are also optionally produced exogenously through biochemical techniques. Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced were members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region ($J_H$) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class. Further, these antibodies are typically produced as antigen binding fragments such as Fab, Fab' F(ab')$_2$, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

The term "selectively binds" as used herein is used contextually, to characterize the binding properties of an antibody. For example, an antibody that binds selectively to a given epitope will bind to that epitope either with greater avidity or with more specificity, relative to other, different epitopes presented by the same molecule, for example at least two fold more efficiently. When used to describe "selectively binds misfolded TTR" for example, an antibody selectively binds misfolded TTR if it binds misfolded TTR, two fold more efficiently than it binds natively folded TTR. In other embodiments, the antibody binds 3-5 fold, 5-7 fold, 7-10 fold, 10-15 fold, 5-15 fold, or 5-30 fold more efficiently. The antibody described in Example 1 selectively binds misfoled TTR but does not bind natively folded TTR even at concentrations as high as 4 micromolar.

The term "part of" as used herein with reference to a peptide molecule for example as shown in SEQ ID NO:1 or an epitope by an antibody described herein, refers to portion of the sequence that retains the epitope activity of binding and/or eliciting an antibody selective for non-native forms of TTR. For example the part is any 4, 5, 6 or 7 contiguous amino acids of SEQ ID NO:1. The antibody is optionally generated by immunizing an animal with an isolated peptide corresponding to said part.

The term "epitope" as used herein means a region of a polypeptide or polypeptide multimer that is recognized by a B cell or T-cell receptor, or an antibody or a binding fragment thereof. The epitope is optionally represented herein by the linear amino acid sequence or the region of the protein recognized by the antibody. An epitope recognized by an antibody can comprise minimally 4 amino acids, 5 amino acids, 6 amino acids, 7 amino acids or 8 amino acids. For example, an epitope as referred to herein can comprise one or more antigenic determinants. For example an antibody generated against an isolated peptide corresponding to TTR residues 89-97 may recognizes part or all of said isolated peptide sequence.

The term "polypeptide" as used herein refers to a sequence of amino acids consisting of naturally occurring residues, and non-naturally occurring residues.

The term "isolated peptide" or "isolated polypeptide" refers to peptide/polypeptide that has been produced, for example, by recombinant or synthetic techniques, and removed from the source that produced the peptide/polypeptide, such as recombinant cells or residual peptide/polypeptide synthesis reactants. The isolated peptide/polypeptide is optionally "purified", which means at least: 80%, 85%, 90%, 95%, 98% or 99% purity and optionally pharmaceutical grade purity.

The term "polynucleotide" and/or "nucleic acid" which are used interchangeably as used herein refers to a nucleic acid molecule comprising nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "isolated nucleic acid" to nucleic acid that has been produced, for example, by recombinant or synthetic techniques, and removed from the source that produced the nucleic acid, such as residual synthesis reactants. The isolated nucleic acid is optionally "purified", which means at least: 80%, 85%, 90%, 95%, 98% or 99% purity and optionally pharmaceutical grade purity.

The term "operatively linked" is intended to mean that the nucleic acid is linked to regulatory sequences in a manner which allows expression of the nucleic acid.

The term "recombinant host cell" is intended to include prokaryotic and eukaryotic cells which have been transformed or transfected with a recombinant expression vector encoding the amyotrophic lateral sclerosis-specific epitopes.

The term "immunogen" as used herein means a substance which provokes an immune response and/or causes production of an antibody.

The term "eliciting an immune response" is defined as initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The term "wild type" as used herein with respect to a polypeptide sequence refers to the primary amino acid sequence of a non-mutant protein, for example having a naturally occurring sequence found in the majority of healthy subjects.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, JD, Higgins DG, Gibson TJ, 1994, *Nucleic Acids Res.* 22(22): 4673-4680), together with BLOSUM 62 scoring matrix (Henikoff S. and Henikoff J. G., 1992, *Proc. Natl. Acad. Sci.* USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch. *J. Mol. Biol.*, 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48:1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations. Computer programs that may be used in this regard include, but are not limited to, GCG (Devereux et al., *Nucleic Acids Res.*, 1984, 12:387) BLASTP, BLASTN and FASTA (Altschul et al., *J. Molec. Biol.*, 1990: 215:403).

The term "natively folded" as used herein with respect to the structure of a polypeptide or polypeptide multimer such as TTR tetramer, refers to the normal folded structure of the polypeptide or multimer. As TTR natively folded is a tetramer, non-natively folded forms on TTR include misfolded TTR tetramer, misfolded TTR monomer and folded TTR monomer including molecules comprising wildtype amino acid sequence and mutations.

The term "misfolded TTR" as used herein refers to the secondary and tertiary structure of a TTR polypeptide monomer or multimer, and indicates that the polypeptide or multimer has adopted a conformation that is not normal for that protein in its properly functioning state. Although TTR misfolding can be caused by mutations in the protein, such as amino acid deletion, substitution, or addition, wild-type sequence protein can also be misfolded in disease, and expose specific epitopes. Misfolded TTR can therefore for example include "mutated misfolded TTR" for example including mutated forms of TTR as disclosed for example in Table 1 and "wild-type misfolded TTR". Mutations in epitope residues 89-97 have been reported. For example, mutations at Glu89 and Ala91 have been reported, Glu89Gln/Lys and Ala91Ser which are conservative mutations. A mutation has also been reported at Ala97 (e.g. Ala97Ser). Optionally, the misfolded and/or monomeric mutant TTR (e.g. detected by the antibody or used in an assay described herein) comprises a mutation that is in a residue outside of amino acids 89-97. For example, optionally the mutation is not at Glu89, Ala91 or Ala97.

The term "animal" or "subject" as used herein includes all members of the animal kingdom including mammals, preferably humans.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Products and Methods

Disclosed herein are antibodies that specifically binds misfolded transthyretin (TTR) multimers and TTR monomers. The antibody, termed misTTR was raised against TTR residues 89-97 (SEQ ID NO:1) which was determined to be an epitope that is buried in the native tetramer and shown to be exposed in the folded and misfolded monomer and multimers comprising the misfolded monomer. The TTR conformation specific antibody detects both pre-fibrillar non-native conformations and TTR amyloid fibrils, but not the native protein. The binding affinity of this antibody to misfolded forms of TTR is less than 10 nanomolar; making possible the development of sensitive immunoassays for the detection of sparsely populated misfolding intermediates. It is also demonstrated herein that nanomolar concentration of the antibody inhibit fibrillogenesis of micromolar concentrations of TTR.

Accordingly, an aspect includes an antibody or binding fragment thereof that specifically binds all or part of EHAEVVFTA (SEQ ID NO:1). EHAEVVFTA corresponds to residues 89-97 of human TTR In an embodiment, the part specifically bound comprises at least 4 or at least 5 or more contiguous amino acids of EHAEVVFTA (SEQ ID NO:1).

As shown in Table 1, mutations are known in TTR including in the region identified in SEQ ID NO:1. In an embodiment, the antibody or binding fragment thereof specifically binds $X_1HX_2EVVFTX_3$ where $X_1$ can be Q or K, $X_2$ can be A or S, and $X_3$ can be G or S (SEQ ID NO:3). In an embodiment, the peptide comprises a sequence of SEQ ID NO:3. In another embodiment, the immunogen, immunoassay, composition method or kit comprises and/or uses a peptide having a sequence of SEQ ID NO:3.

As mentioned above, an epitope as referred to herein can comprise one or more antigenic determinants. For example an antibody generated against an isolated peptide corresponding to TTR residues 89-97 may recognize part or all of said isolated peptide sequence. Accordingly, the part is an antigenic determinant. In an embodiment, the part comprises at least 5 contiguous amino acids, at least 6 contiguous amino acids, at least 7 contiguous amino acids or at least 8 contiguous amino acids of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, antibody or binding fragment thereof specifically binds a misfolded conformation of TTR. In yet another embodiment, the antibody or binding fragment thereof specifically binds monomeric TTR. In another embodiment, the antibody or binding fragment thereof specifically binds TTR fibrils.

The misfolded TTR and/or monomeric TTR specifically bound by the antibody can have wild-type sequence or comprise a mutation for example as disclosed in Table 1. Optionally the mutation is a mutation in an amino residue not including amino acid residues corresponding to amino acids 89-97. Monomeric TTR can have a folded conformation or a misfolded conformation as the epitope is available in the monomeric natively folded conformation. The monomeric form can also be mutated and/or misfolded.

TABLE 1

Amyloidogenic TTR Mutations

| Mutation | Clinical Features | Origin |
|---|---|---|
| Cys10Arg | PN, AN, Eye | Hungary |
| Leu12Pro | LM, PN, AN | UK |
| Asp18Glu | PN, AN | Columbia |
| Asp18Gly | LM | Hungary |
| Val20Ile | Heart | Germany |
| Ser23Asn | Heart | Portugal |
| Pro24Ser | Heart, CTS, PN | USA |
| Val28Met | PN, AN | Portugal |
| Val30Met | PN, AN, Eye | Several |
| Val30Ala | Heart, AN | Germany |
| Val30Leu | PN, AN | Japan |
| Val30Gly | LM, Eye | France |
| Phe33Ile | PN, Eye | Poland |
| Phe33Leu | PN, AN | Poland |
| Phe33Val | PN, AN | UK |
| Arg34Thr | PN, Heart | Italy |
| Lys35Asn | PN, AN, Heart | France |
| Ala36Pro | PN, Eye | Greece |
| Asp38Ala | PN, Heart | Japan |
| Glu42Gly | PN, AN | Japan |
| Glu42Asp | Heart | France |
| Phe44Ser | PN, AN, Heart | Ireland |
| Ala45Asp | Heart | Italy |
| Ala45Ser | Heart | Sweden |
| Ala45Thr | Heart | Italy |
| Gly47Arg | PN, AN | Japan |
| Gly47Ala | Heart, PN, AN | Italy |
| Gly47Val | PN, AN, Heart | Sri Lanka |
| Gly47Glu | PN | Germany |
| Thr49Ala | Heart, PN | Italy |
| Thr49Ile | PN, Heart | Japan |
| Ser50Arg | PN, AN | Japan |
| Ser50Ile | Heart, PN, AN | Japan |
| Glu51Gly | Heart | USA |
| Ser52Pro | PN, AN, Heart | UK |
| Gly53Glu | LM, Heart | France |
| Glu54Gly | PN, AN | UK |
| Glu54Lys | PN, AN, Heart | Japan |
| Leu55Arg | LM, PN | Germany |
| Leu55Pro | PN, Heart, AN | Taiwan |
| His56Arg | Heart | USA |
| Leu58His | CTS, Heart | Germany |
| Leu58Arg | CTS, AN, Eye | Japan |
| Thr59Lys | Heart, PN | Itlay |
| Thr60Ala | Heart, CTS | Ireland |
| Glu61Lys | PN | Japan |
| Phe64Leu | PN, CTS, Heart | Italy |
| Phe64Ser | LM, PN, Eye | Italy |
| Ile68Leu | Heart | Germany |
| Tyr69His | Eye | Scotland |
| Lys70Asn | CTS, PN, Eye | Germany |
| Val71Ala | PN, Eye | Spain |
| Ile73Val | PN, AN | Bangladesh |
| Ser77Phe | PN | France |
| Ile84Ser | Heart, CTS, Eye | Switzerland |
| Ile84Asn | Eye, Heart | Italy |
| Ile84Thr | Heart, PN, AN | Germany |
| Glu89Gln | PN, Heart | Italy |
| Gku89Lys | PN, Heart | USA |
| Ala91Ser | PN, CTS, Heart | France |
| Ala97Ser | PN, Heart | France |
| Ile107Val | Heart, CTS, PN | Germany |
| Ile107Met | PN, Heart | Germany |
| Ala109Ser | PN | Japan |
| Leu111Met | Heart | Denmark |
| Ser112Ile | PN, Heart | Italy |
| Tyr114Cys | PN, AN, Eye | Japan |
| Tyr114His | CTS | Japan |
| Tyl116Ser | PN, CTS | France |

TABLE 1-continued

Amyloidogenic TTR Mutations

| Mutation | Clinical Features | Origin |
|---|---|---|
| Ala120Ser | Heart, PN, AN | Africa |
| Val122Ile | Heart | Africa |
| Val122del | Heart, PN, CTS | Equador/Spain |
| Val122Ala | Heart, Eye, PN | UK |

AN, autonomic neuropathy;
CTS, carpal tunnel syndrome;
Eye, vitreous deposition;
PN, peripheral neuropathy;
LM, leptomeningeal amyloid;
Heart, cardiomyopathy.

In another embodiment, the antibody or binding fragment thereof is capable of disrupting or reducing TTR fibril formation when monomeric TTR or misfolded TTR intermediates in solution is/are contacted with the antibody or binding fragment.

In another embodiment, a substochiometric amount of antibody or binding fragment thereof compared to TTR tetramer and TTR monomer is required to disrupt or reduce TTR fibril formation.

In another embodiment, the antibody is a monoclonal or polyclonal antibody.

In yet another embodiment, the antibody is chimeric or humanized antibody.

In a further embodiment, the antibody fragment is a Fab, Fab', F(ab')$_2$, scFv, dsFv, ds-scFv, dimer, minibody, diabody, or multimer thereof or a bispecific antibody fragment.

In an embodiment, the antibody is isolated.

In another embodiment, the antibody is purified optionally affinity purified.

Methods of producing an antibody are also provided.

To produce monoclonal antibodies, antibody producing cells (lymphocytes) can be harvested from a subject immunized with an immunogen comprising a peptide corresponding to all or part of SEQ ID NO:1 or 3, the part comprising at least 4 or at least 5 or more contiguous amino acids of SEQ ID NO:1 or 3, and optionally comprising one or more linkers (e.g. SEQ ID NO: 2) and fused with myeloma cells by standard somatic cell fusion procedures thus immortalizing these cells and yielding hybridoma cells. Such techniques are well known in the art, (e.g. the hybridoma technique originally developed by Kohler and Milstein (Kohler and Milstein *Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121:140-67 (1986)), and screening of combinatorial antibody libraries (Huse et al., *Science* 246:1275 (1989)). Hybridoma cells can be screened immunochemically for production of antibodies specifically reactive with the TTR epitope and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al. *Nature* 341:544-546 (1989); Huse et al. *Science* 246:1275 (1989); and McCafferty et al. *Nature* 348:552-554 (1990)).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Additionally, antibodies specific for the sequence shown in SEQ ID NO: 1 and/or 3 are readily isolated by screening antibody phage display libraries. For example, an antibody phage library is optionally screened by using a peptide comprising all or part of the sequence shown in SEQ ID NO: 1 or 3 to identify antibody fragments specific for epitope. Antibody fragments identified are optionally used to produce a variety of recombinant antibodies that are useful with different embodiments disclosed herein. Antibody phage display libraries are commercially available, for example, through Xoma (Berkeley, Calif.) Methods for screening antibody phage libraries are well known in the art.

Further methods are described below for example in Example 2 which can be used to produce polyclonal antibodies.

Also provided in another embodiment, is an isolated peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3), the part comprising at least 4, or at least 5 or more contiguous amino acids.

The isolated peptide can be labelled with a detectable label, or coupled to one or more linkers or tags.

In an embodiment, the isolated peptide further comprises one or more amino acid linkers coupled to one or more of the peptide N and/or C termini.

The linker can for example comprise from about 1 amino acid to about 5 or any number of residues in between. In an embodiment, the linker comprises 2, 3, 4, or 5 amino acid residues.

The linker for example can allow the peptide to be coupled tandemly to another copy of the same or a different peptide corresponding to the same or a different epitope.

In another embodiment, the amino acid linkers include one or more G or K or S residues and for example the amino acid linker or linkers each independently comprise GG or GGKG. Glycine-serine linkers can also be used.

In another embodiment, the isolated peptide comprises all or part of GGEHAEVVFTAGGKG (SEQ ID NO:2).

In an embodiment, the isolated peptide is synthesized using Fmoc protected amino acids. Further details are provided for example in Example 2.

In another embodiment, the isolated peptide is specifically recognized by an antibody described herein.

A further aspect comprises an isolated peptide comprising a peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3) coupled to a tag or detectable label.

The tag can for example be a polyHIS or FLAG tag, GST, GFP or other tag known in the art.

The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the detectable signal is detectable indirectly. For example, a secondary antibody that is specific for an antibody described herein and contains a detectable label can be used to detect the antibody.

A further aspect is an isolated nucleic acid encoding the isolated peptide described herein.

A further aspect includes a host cell comprising a nucleic acid described herein. In an embodiment, the nucleic acid is operatively linked to a promoter. In an embodiment, the host cell expresses a recombinant peptide comprising all or part of EHAEVVFTA (SEQ ID NO:1) or other peptide described herein.

Also included in another aspect is an immunogen, comprising a peptide, the peptide comprising all or part of EHAEVVFTA(SEQ ID NO:1) and/or $X_1HX_2EVVFTX_3$ where $X_1$ can be Q or K, $X_2$ can be A or S, and $X_3$ can be G or S (SEQ ID NO:3). The immunogen in an embodiment comprises the peptide fused to a linker or tag. The immunogen for example can comprise the TTR peptide (e.g. comprising all or part of SEQ ID NO:1 and/or SEQ ID NO:3) or the isolated peptide coupled to a tag (e.g. a fusion protein) described herein in forms useful to raise antibodies. For example the peptide can be labelled, be coupled to a linker or other molecule, for example for enhancing immunogenicity.

In an embodiment, the immunogen comprises an immunogenicity enhancing molecule or solubility enhancing molecule optionally coupled to the peptide.

In an embodiment, the immunogenicity enhancing molecule is keyhole limpet hemocyanin (KLH), albumin or a multiple antigenic peptide dendrimer.

In another embodiment, the immunogen comprises one or more linkers.

Amino acid linkers can be added for example to permit tandem peptide coupling to another copy of the same or a different peptide corresponding to the same or a different epitope. In another embodiment, the one or more linkers is/are amino acid linkers conjugated to one or more of the peptide N and/or C termini.

In another embodiment, each linker comprises one or more amino acid residues, wherein the amino acid residues selected from glycine and/or lysine.

The linker can for example be 2 to 5 residues in length.

In yet another embodiment, the linker or linkers each selected independently comprise GG or GGKG.

In a further embodiment, the peptide linker conjugate sequence is GGEHAEVVFTAGGKG (SEQ ID NO:2). The linker can for example be added to a part of the peptide having sequence shown in SEQ ID NO:1 or 3. For example, the linker can be attached to a peptide comprising amino acids 2-8, 3-8, 1-7, 1-6. 2-7, 2-6 or other peptides comprising at least 4 or at least 5 or more contiguous amino acids of SEQ ID NO:1

The immunogen for example comprising peptides fused to a tag (alternatively referred to as fusion proteins) can be for example up to 50 amino acids, 100 amino acids or larger.

In another embodiment, the immunogen comprises multiple peptides each peptide comprising all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3), wherein the multiple peptides are synthesized as a multiple antigenic peptide (MAP). A MAP is a branched poly-lysine dendrimer. Multiple epitope peptides are attached for example to one or both of the amino terminus and side-chain of the lysines. In an embodiment, the peptides on a MAP dendritic core are attached to Wang resin.

In another embodiment, the immunogen is capable of eliciting production of an antibody that specifically binds all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, the immunogen is used to producing an antibody that that specifically binds all or part of EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, wherein the antibody produced specifically binds a misfolded or monomeric TTR conformation.

A further aspect includes a composition comprising an antibody, isolated peptide, isolated nucleic acid or an immunogen described herein and a suitable carrier, diluent or vehicle.

Suitable vehicles are described, for example, in Remington's Pharmaceutical Sciences (17). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Suitable include essentially chemically inert and nontoxic compositions that do not interfere with the effectiveness of the biological activity of the composition. Examples of suitable carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes.

In an embodiment, composition comprises the isolated peptide, or immunogen and further comprises an adjuvant.

Immunogenicity can be improved if the immunogen or composition comprising the immunogen comprises an adjuvant. Commonly, adjuvants are used as a 0.05 to 1.0 percent solution in phosphate-buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses.

Examples of adjuvants include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes. Others include aluminum compounds (such as aluminum hydroxide, aluminum phosphate, and aluminum hydroxy phosphate), bacterial toxins (e.g., the cholera toxin (CT), the E. coli heat-labile toxin (LT), the Clostridium difficile toxin A and the pertussis toxin (PT), or combinations, subunits, toxoids, or mutants thereof).

In another embodiment, the adjuvant is selected from Freund's complete and incomplete adjuvant.

A further aspect includes an immunoassay comprising an antibody described herein.

In an embodiment, the immunoassay is an ELISA.

Also provided is a kit, comprising an isolated antibody, isolated peptide, isolated nucleic acid, immunogen, composition and/or immunoassay described herein, and a vessel such as a vial for housing the antibody, isolated peptide, isolated nucleic acid, immunogen and/or composition.

In another embodiment, the kit further comprises instructions for use in a method described herein.

The kit can comprise a recombinant protein for example recombinant TTR or a fragment thereof. The TTR can be recombinantly produced according to methods known in the art including the method described for example in Example 2.

Also included in other aspects are uses of the antibodies, isolated peptides, isolated nucleic acids, recombinant host cells, immunogens, compositions, immunoassays, kits described herein, for example for use for a method described herein.

A further aspect includes a method for preparing an antibody, the method comprising immunizing a non-human subject with an immunogen or composition described herein.

In an embodiment, the method further comprises isolating an antibody that specifically binds EHAEVVFTA (SEQ ID NO:1) and/or $X_1HX_2EVVFTX_3$ where $X_1$ can be Q or K, $X_2$ can be A or S, and $X_3$ can be G or S (SEQ ID NO:3).

In another embodiment, the method further comprises forming antibody-producing hybridomas.

Another aspect includes a method of detecting a misfolded TTR conformation and/or monomeric TTR in a test sample, the method comprising contacting the test sample with an antibody or binding fragment described herein under conditions suitable to form a specific antibody antigen complex between the antibody and TTR; determining if a specific antibody TTR complex is formed thereby detecting misfolded TTR and/or monomeric TTR in the test sample.

In an embodiment the method is for detecting a misfolded TTR conformation in a test sample, the method comprising contacting the test sample with an antibody or binding fragment described under conditions suitable to form a specific antibody antigen complex between the antibody and TTR; determining if a specific antibody TTR complex is formed thereby detecting misfolded TTR in the test sample.

In another embodiment, the method is for detecting monomeric TTR in a test sample, the method comprising contacting the test sample with an antibody or binding fragment described herein under conditions suitable to form a specific antibody TTR complex between the antibody and TTR; determining if a specific antibody TTR complex is formed thereby detecting monomeric TTR in the test sample.

In an embodiment, the misfolded TTR is comprised in TTR fibrils.

The misfolded TTR and/or monomeric TTR detected by the antibody can have wild-type sequence or comprise a mutation for example as disclosed in Table 1. Monomeric TTR can have folded conformation as the epitope is available in the monomeric folded conformation. The monomeric form can also be mutated and/or misfolded.

In another embodiment, the determining comprises measuring the amount of the antibody-antigen complex in the test sample and comparing the amount of antibody-antigen complex in the test sample to a control, wherein a difference in the amount of antibody-antigen complex in the test sample as compared to the control is indicative that misfolded TTR is detected in the test sample.

The control can be for example a sample comprising natively folded TTR, for example a preparation of the same type as the test sample comprising natively folded TTR.

A person skilled in the art will appreciate that a number of methods can be used to determine if misfolded TTR is present in a sample using the antibodies described herein, including immunoassays such as flow cytometry, Western blots, dot blots, ELISA, and immunoprecipitation followed by SDS-PAGE immunocytochemistry. Examples of methods that can be used, for example dot blots and ELISAs, are provided in Example 2 below. For example the antibodies immunoassays, cells isolated peptides etc. described herein can be used in the methods to determine if misfolded and/or monomeric TTR is present in the sample.

In another embodiment, the method is for detecting misfolded TTR and/or monomeric TTR in a subject with an unknown neuropathy or a subject suspected and/or known to have an amyloid deposition disease.

Another aspect includes a method of diagnosing a subject with an amyloid deposition disease, the method comprising detecting misfolded TTR and/or monomeric TTR as described herein.

In an embodiment, the method comprises contacting a sample obtained from the subject with an antibody or binding fragment described herein under conditions suitable to form a specific antibody antigen complex between the antibody and TTR; determining if a specific antibody antigen complex is formed; and identifying the subject when specific binding is detected as having or having an increased risk of developing an amyloid deposition disease.

In an embodiment, the amyloid deposition disease is a TTR amyloid deposition disease (e.g. TTR amyloidoses). In an embodiment, the amyloid TTR amyloidosis disease is selected from systemic senile amyloidosis, familial amyloid polyneuropathy, and familial amyloid cardiomyopathy.

In another embodiment, the test sample is a biological sample obtained from a subject.

In another embodiment, the sample comprises blood, serum, plasma, and/or solid tissue.

At present, the diagnosis of transthyretin amyloidoses typically relies on target organ biopsies, followed by histological staining of the excised tissue with the amyloid specific dye Congo red. Should a positive test for amyloid be given, immunohistochemical staining for transthyretin is subsequently performed to ensure that the precursor protein responsible for amyloid formation is indeed transthyretin. For familial forms of the disease, demonstration of a mutation in the gene encoding transthyretin is needed, in addition to the aforementioned staining procedures, before diagnosis can be made.

In an embodiment, the method further performing one or more of these diagnostic methods, for example as conformation of diagnosis.

Also provided is a method of inhibiting TTR fibril formation, the method comprising contacting an antibody or fragment disclosed herein with misfolded TTR or monomeric TTR under fibril formation conditions, wherein the antibody specifically binds the misfolded and/or monomeric TTR and inhibits fibril formation.

It is demonstrated herein that antibodies that bind the 89-97 TTR epitope can inhibit fibril formation in solution. As demonstrated herein, antibodies that bind native TTR do not possess such fibril inhibition properties. Without wishing to be bound to theory, the antibody may target an aggregation nucleus and specifically binds misfolded intermediates thereby preventing fibril formation.

In an embodiment, the antibody or binding fragment is contracted with misfolded TTR or monomeric TTR during the lag phase of fibril formation.

The assay can be used for example to screen for competing antibodies.

A further aspect is a screen for identifiying a TTR stabilizer, the method comprising: a) contacting an antibody or fragment disclosed herein that selectively binds misfolded and/or monomeric TTR with misfolded TTR and/or monomeric TTR in a test solution under fibril formation conditions with the test solution comprising either i) a test compound and ii) absence of the test compound;
b) measuring TTR fibril formation in i) and ii) and;
c) identifying the test compound as a TTR stabilizer if the test compound increases TTR fibril formation compared to the absence of the test compound.

Figure 5A:
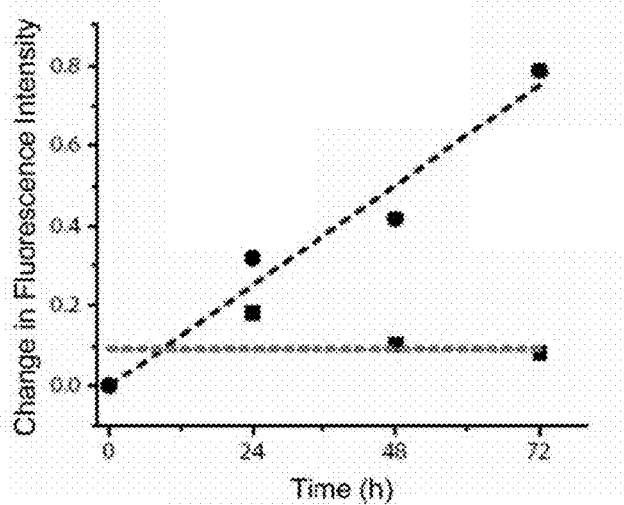
FIGS. 5A and 5B: misTTR antibody inhibits TTR fibrillogenesis in vitro.

As described below, an amyloid specific dye ThT was used to assess the extent of fibril formation every 24 hours, for 3 consecutive days. In the absence of the misTTR antibody, an enhanced ThT fluorescence was observed over the course of the experiment; an observation consistent with the occurrence of amyloid formation (FIG. 5a). However, in the presence of the misTTR antibody, no significant changes in ThT fluorescence was observed (FIG. 5a); an indication that the presence of the misTTR antibody likely disrupts amyloid formation.

Figure 5B:
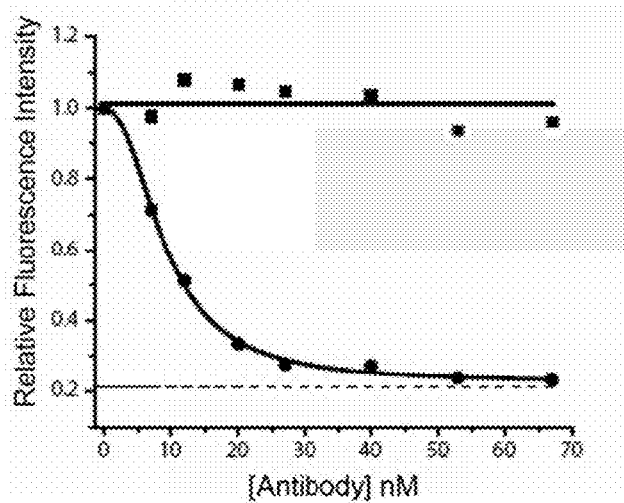

To investigate this inhibitory effect, physiological concentrations of TTR were left under fibril formation conditions; however this time, in the presence of various concentrations of the misTTR antibody. After 72 hours, ThT was used to assess the extent of fibrillogenesis. Strikingly, a dose dependent inhibition of TTR fibrillogenesis was observed with the antibody concentrations tested (EC50=9 nM). Substoichiometric concentrations of the misTTR antibody were sufficient to suppress TTR fibrillogenesis in vitro (FIG. 5b)

The extent of fibril formation for example can probed by turbidity measurements for example at 400 nm on a Jasco V-500 UV-visible spectrometer equipped with a temperature control unit. Thioflavin-T can also be used to assess the extent of amyloid fibril formation. For example, a five-fold molar excess of Thioflavin-T can be added to transthyretin samples and left at room temperature for 30 minutes before measurements are taken. Thioflavin-T fluorescence can be monitored using a Photon Technology International C60 spectrofluorimeter as described in the Examples.

he above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Both wild-type and mutant transthyretin (TTR) can misfold resulting in amyloid deposition disease involving either the heart or peripheral nerves. In vitro generated TTR misfolding intermediates were targeted and amyloid inhibition at substoichiometric concentrations was achieved. An antibody, termed misTTR was developed, which targets transthyretin residues 89-97; an epitope that is buried in the native tetramer but exposed in the misfolded monomer. Nanomolar concentrations of misTTR are demonstrated to inhibit fibrillogenesis of micromolar concentrations of TTR. Commercially available antibodies that bind native TTR do not possess such fibril inhibition properties. It is demonstrated that misTTR targets a critical aggregation nucleus, thus demonstrating that selective targeting of misfolded intermediates is possible.

Example 2

Results
Design and Characterization of Antibody

The use of antibodies, particularly as structural probes, to investigate the misfolding pathway of amyloidogenic and non-amyloidogenic proteins has been applied in the study of several protein misfolding diseases[5-7]. In the case of TTR amyloidoses, the generation of such antibodies have often relied on highly destabilized mutant proteins or randomly generated linear sequences of the molecule[8-10]. Here, rational design based on known X-ray crystal structures of TTR and biochemical data on the misfolding pathway was used to produce a conformation specific antibody that could be used not only as a structural probe, but an agent that targets sparsely populated misfolding intermediates of TTR.

Figure 2A:
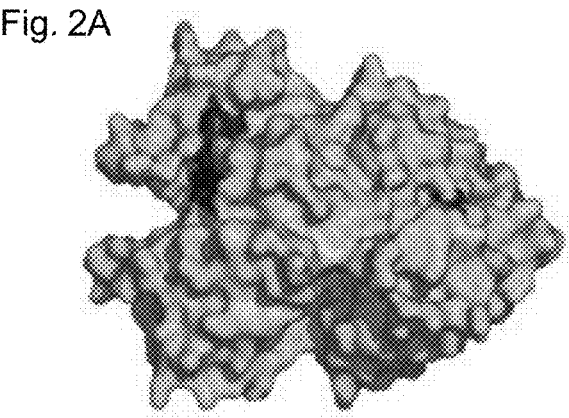
FIGS. 2A and 2B: Structure-guided design of antibody.
Figure 2B:
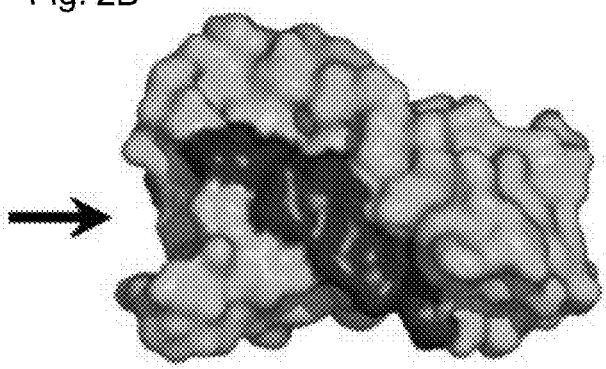

Native TTR exists as a dimer of dimers forming a stable homotetramer under normal conditions. However, during amyloid formation, it undergoes obligate monomerization. Examination of the X-ray crystal structure of TTR revealed that residues 89-97, located in the F strand, are sequestered at the dimer interface of the protein and inaccessible in native tetramer (FIG. 2a). It was reasoned that an antibody raised to an epitope encompassing these residues would selectively recognize misfolded conformations of TTR in which the dimer interface is disrupted and exposed, such as monomers (FIG. 2b), non-native oligomers, or fibrils. For brevity, this antibody is referred to as the misTTR (misfolded conformations of TTR) antibody. A multiple antigenic peptide (MAP) was synthesized where each branch of the dendritic core contained the sequence ggEHAEVVFT-Aggkg (SEQ ID NO. 2); the capitalized sequences represent residues 89-97 of TTR. Gly-Lys linkers were added to the N and C termini so the peptide epitope would resemble an internal sequence as well as to increase the molecular weight and solubility of the MAP antigen for an enhanced immune response. Rabbit anti-sera produced from immunization with the MAP antigen were affinity purified from the cognate linear peptide and used in the experiments described herein.

Figure 3A:
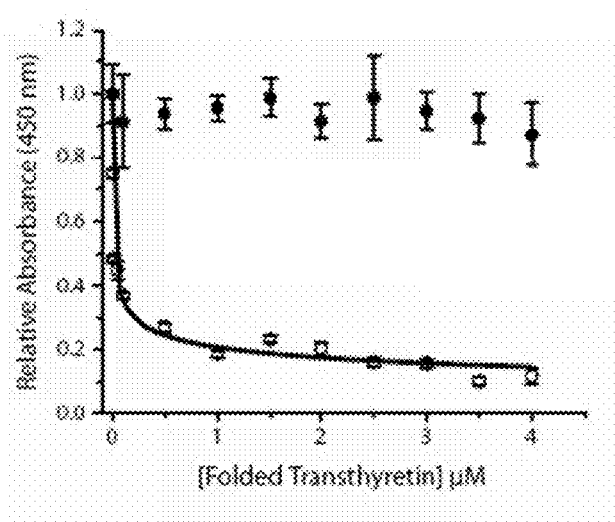
FIGS. 3A and 3B: misTTR antibody selectively binds monomeric, misfolded conformations of TTR.
Figure 3B:
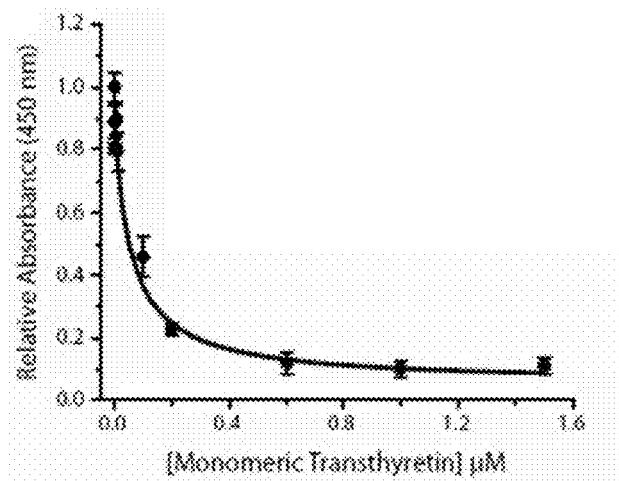

The selectivity of the misTTR antibody was tested using a competition enzyme linked immunosorbent assay (ELISA). Since TTR in solution closely resembles the physiological condition, the competitive binding of the antibody to antigens was evaluated in solution and to those adsorbed to the polystyrene matrix. Folded TTR in solution was unable to compete with guanidine hydrochloride (GdnHCl) unfolded TTR on the ELISA plate for antibody binding at any concentration tested (FIG. 3a). As a control, the assay was also performed using a commercially available (non-selective) anti-TTR antibody (Sigma Aldrich), which was raised to native-folded tetrameric TTR. As expected, folded TTR was able to compete for antibody binding when the pan-specific antibody was used (FIG. 3b).

Since tetramer dissociation into a monomeric, amyloid competent intermediate is required for fibril formation, it was sought to determine whether the misTTR antibody would recognize this intermediate in vitro. While the misTTR antibody did not bind to folded TTR, it was able to bind to stable preparations of monomeric TTR in solution. Using previously established conditions to generate the monomeric amyloidogenic intermediate[11-12], it was found that the misTTR antibody was able to bind to this intermediate with an EC50 value of 63 nM (FIG. 3b). Despite conformational changes known to occur within TTR monomers immediately following tetramer dissociation[11, 13-15], the epitope remained accessible for antibody binding. The differential reactivity of the misTTR antibody to bind monomeric or unfolded TTR but not native TTR confirms that the selected epitope is indeed buried in the native fold of the protein, but exposed in the amyloidogenic intermediate.

Figure 4A:
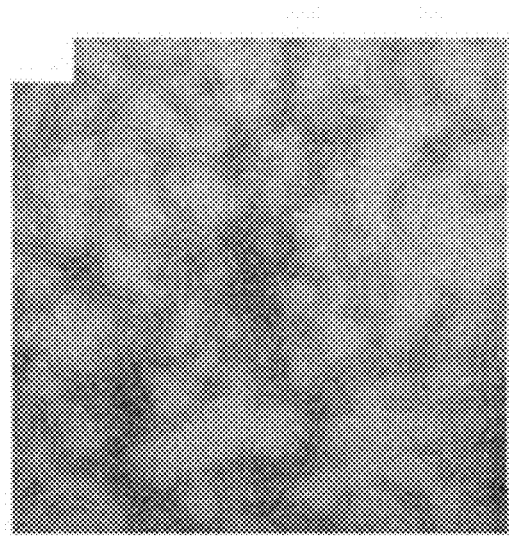
FIG. 4A-C: Recognition of TTR amyloid fibrils by misTTR antibody.
Figure 4B:
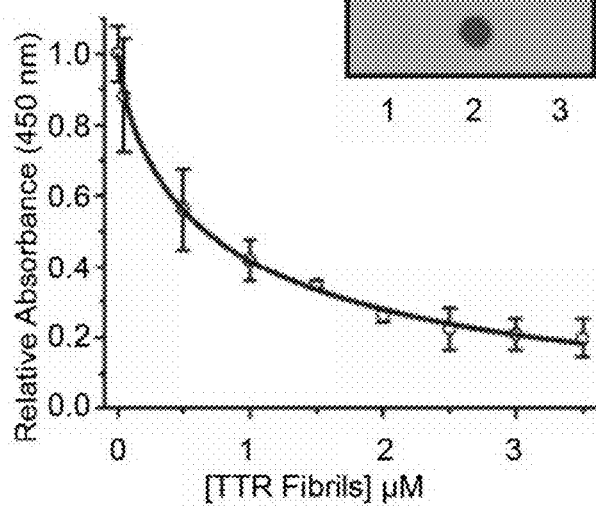
Figure 4C:
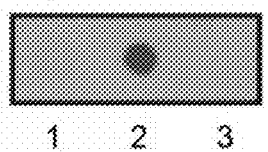

The reactivity of the misTTR antibody was evaluated with TTR amyloid fibrils formed in vitro. TTR readily misfolds and assembles into amyloid fibrils under physiologically relevant conditions (pH 4.5, 37° C., 3 days)[11]. The aggregates formed under these conditions were able to bind the amyloid specific dye thioflavin T (ThT), causing an enhancement in the fluorescence emission of the dye as well as a characteristic red shift in its emission spectrum. The aggregates were also confirmed to consist primarily of fibrils, ~7 nm in diameter, with a morphology consistent with previously published reports of fibrillar structures formed by other amyloidogenic proteins[16-17] (FIG. 4a). To determine whether the misTTR antibody would recognize TTR fibrils formed in vitro, a competition ELISA was performed. Suspended TTR fibrils were able to compete with unfolded TTR on the ELISA plate for antibody binding (FIG. 4b). The antibody also discriminates between native tetrameric TTR and TTR fibrils in a direct binding assay such as a dot blot (FIG. 4c). The misTTR antibody thus meets its design specifications for selective reactivity with misfolded conformations of TTR.

Substoichiometric Amounts of misTTR Antibody Suppresses TTR Fibrillogenesis In Vitro Studies have shown that to transform into amyloid fibrils, TTR must first dissociate into its monomeric subunits. However, the dissociation of TTR to normally folded monomers, while necessary, is not sufficient for fibril formation. Each monomer undergoes a conformational change in order to facilitate self-assembly into amyloid fibrils. Since the misTTR antibody is able to recognize monomeric TTR in solution (FIG. 3b), it was hypothesized that under fibril formation conditions, the binding interaction between the misTTR antibody and monomeric TTR could disrupt TTR self-assembly or alter the fibrillogenesis process. To investigate this notion, physiological concentrations of TTR were left under fibril formation conditions in the presence and absence of the misTTR antibody. The amyloid specific dye ThT was used to assess the extent of fibril formation every 24 hours, for 3 consecutive days. In the absence of the misTTR antibody, an enhanced ThT fluorescence was observed over the course of the experiment; an observation consistent with the occurrence of amyloid formation (FIG. 5a). However, in the presence of the misTTR antibody, no significant changes in ThT fluorescence was observed (FIG. 5a); an indication that the presence of the misTTR antibody likely disrupts amyloid formation.

To investigate this inhibitory effect, physiological concentrations of TTR were left under fibril formation conditions; however this time, in the presence of various concentrations of the misTTR antibody. After 72 hours, ThT was used to assess the extent of fibrillogenesis. Strikingly, a dose dependent inhibition of TTR fibrillogenesis was observed with the antibody concentrations tested (EC50=9 nM). Substoichiometric concentrations of the misTTR antibody were sufficient to suppress TTR fibrillogenesis in vitro (FIG. 5b). To confirm that the observed inhibitory effect is a consequence of the design and selectivity of the misTTR antibody, the experiment was repeated using the commercially available anti-TTR antibody. The commercial antibody, which was raised to native tetrameric TTR, had no effect on TTR fibrillogenesis, as assessed by ThT (FIG. 5b); it could neither stabilize the native fold of TTR nor prevent the dissociation and self-assembly of TTR into amyloid fibrils under the conditions used. As such, it was proposed that the inhibition of TTR fibril formation is not a generic feature of antibodies, but likely stems from the design, specificity, and ability of the misTTR antibody to recognize monomeric, misfolded conformations of TTR present in the fibrillogenesis pathway.

misTTR Antibody Extends Lag Phase of the TTR Fibrillogenesis Process

Figure 6:
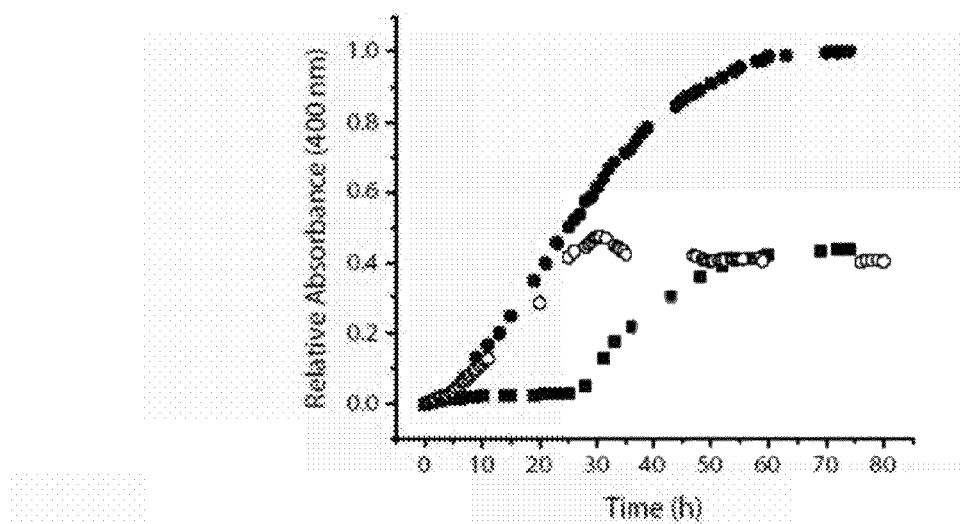
FIG. 6: Effects of substoichiometric amounts of misTTR antibody on TTR fibrillogenesis. Timecourse of TTR fibril formation, in the absence (filled circles) and presence (filled squares) of 27 nM of the misTTR antibody, monitored by turbidity measurements. Unfilled circles depict the effect of 27 nM of the misTTR antibody added at the 30-hour mark, during TTR fibril growth.

To understand the mechanism by which substoichiometric amounts of the misTTR antibody suppress TTR fibril formation, the kinetics of the process was evaluated using UV/VIS absorbance spectroscopy. A time course of TTR fibril formation revealed what appeared to be a nucleated polymerization mechanism, which is consistent with previously published reports[11, 18]. A lag phase, corresponding to the length of time needed to form stable nuclei, was observed followed by a rapid growth phase, which began to plateau after 60 hours (FIG. 6). In the presence of the misTTR antibody, a change in the kinetic profile of TTR fibrillogenesis occurred. An extension of the lag phase, from 2-5 hours to 30 hours, was observed along with a 60 percent reduction in the amount of aggregates present (FIG. 6). These aggregates are likely to be prefibrillar species as they did not react with ThT.

Although the misTTR antibody was able to prolong the lag phase of TTR fibril formation, it was also looked to determine if it would have an effect when incubated with TTR during the polymerization or growth phase of fibrillogenesis. The addition of substoichiometric amounts of the misTTR antibody during the polymerization phase resulted in a slight decrease of the absorbance signal over a span of about 5 hours (FIG. 6). While this slight decrease could be attributed to a dilution effect, this is highly unlikely due to the volume of antibody added. Since the observed signal decrease was gradual, it is likely that a slight disaggregation of prefibrillar species took place upon addition of the misTTR antibody. Irrespective of the mode of action by which the antibody exerts its effect, a complete inhibition of TTR fibrillogenesis was observed following the addition of substoichiometric amounts of the antibody during the polymerization phase (FIG. 6).

Discussion

Using a structure-guided approach, an antibody that is able to distinguish between native and misfolded conformations of TTR have been designed. The findings, which indicate that this antibody prevents the progression to amyloid fibril formation at sub[11] stoichiometric levels, suggest that the antibody binds sparsely populated misfolded intermediates. The advantage of this approach of targeting sparsely populated misfolded species is that low concentrations of therapeutic agents can be used for efficacious outcomes.

While the results of the assays used highlight the ability of the misTTR antibody to recognize TTR amyloid fibrils formed in vitro (EC50=0.8 μM), the core structure of amyloid fibrils formed in vitro may differ significantly from that formed in vivo. It is plausible that the presence of accessory proteins such as serum amyloid P component and gylcosaminoglycans, which are generally associated with amyloid fibrils derived from patients, may affect the accessibility of the selected epitope. Although additional experiments with pathological tissue samples are needed to confirm these results, the available data suggests that the selected epitope does not participate in the formation of the core structure of TTR fibril. The F-strand or a segment of the F-strand encompassing the selected epitope is likely exposed in the fibrillar form of TTR.

Figure 7:
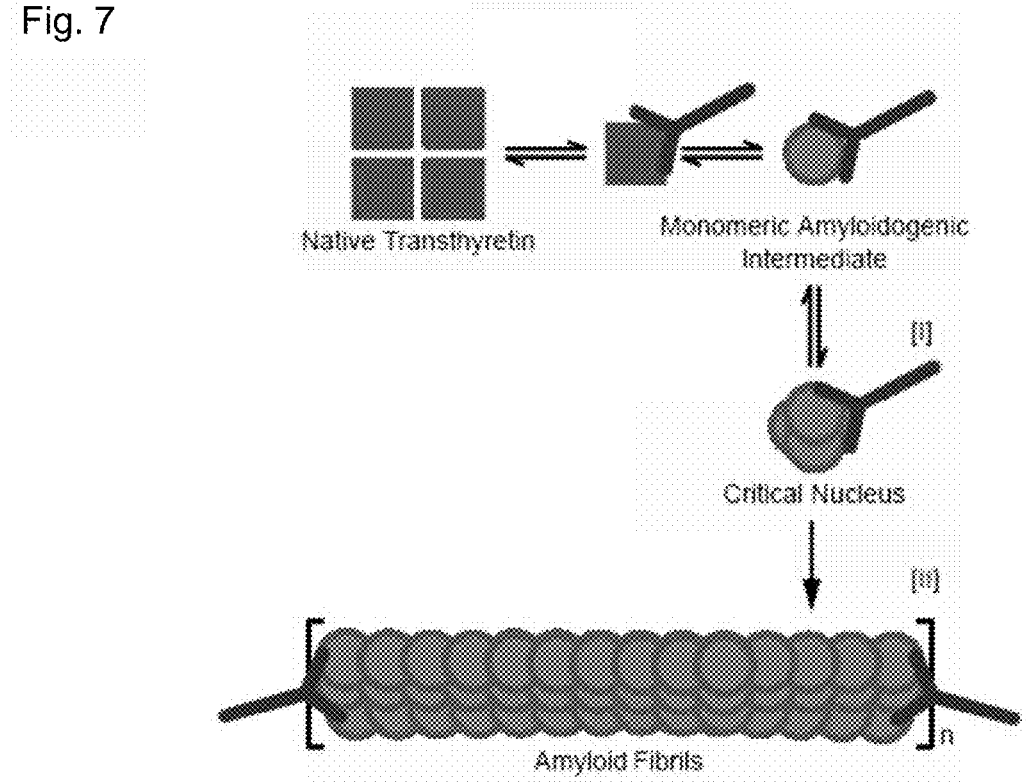
FIG. 7: Proposed model for the detection of misfolded TTR molecules by the misTTR antibody. During the fibril formation process, native tetrameric TTR first dissociates into an altered monomeric intermediate. This altered monomeric intermediate self assembles into stable nuclei, which allows for fibril formation to proceed. Substoichiometric amounts of the misTTR antibody likely binding misfolded conformations of TTR that comprise the monomeric TTR and critical nuclei, which are likely present at very low concentrations. The misTTR antibody may also bind TTR amyloid fibrils.

The proposed mechanism by which the misTTR antibody inhibits TTR fibrillogenesis is illustrated in FIG. 7. Based on the data collected, it was suspected that the substoichiometric amounts of the misTTR antibody may act to suppress TTR fibrillogenesis in one of two ways. The first is as a disrupter of nuclei formation. During the course of fibrillogenesis, several TTR subunits associate to form a core or nucleus before cooperative growth can occur. However, since the association of subunits into a nucleus is an energetically unfavourable process, the lag phase generally persists for a period of time until a stable nucleus is formed. At a molar ratio of ~1:130 (antibody to TTR), the misTTR antibody likely binds to small, oligomeric structures populated during the lag phase to delay the onset of polymerization. Binding to such structures may either occlude surfaces required for polymerization or impede the assembly of stable nuclei needed for fibril growth. A second way by which the misTTR antibody may act to suppress TTR fibrillogenesis is by acting as a lid or cap. At substoichiometric concentrations, the misTTR antibody may prevent fibril formation by capping the ends of prefibrillar species. This mode of action is more likely as significantly lower concentrations of the misTTR antibody would be required.

Materials and Methods

Antibody Generation

To generate the misTTR antibody, peptide synthesis was carried out using standard fluorenylmethoxycarbonyl (Fmoc)-based chemistry on a PS3 Automated Solid Phase Peptide Synthesizer (Protein Technologies Inc). A MAP with the following sequence, GGEHAEVVFTAGGKG (SEQ ID NO: 2), was synthesized on an [Fmoc-Lys(Fmoc)]4-Lys2-Lys-βAla-Wang resin (Advanced ChemTech, SM5102) using Fmoc-protected amino acids (Advanced ChemTech, Applied Biosystems, and Novabiochem). The peptide was subsequently cleaved from the resin with a mixture consisting of 90% trifluoroacetic acid, 8% anisole, and 2% triisopropylsilane (all from Sigma Aldrich) and purified using ether extractions of protecting groups and scavengers; peptide composition was verified using amino acid analysis. The MAP was then sent to Sigma-Genosys for rabbit antiserum production, which followed standard protocol (Sigma-Genosys) and was in accordance with the Animal Welfare Act (USA).

Antibody Purification

To purify the misTTR antibody from rabbit antiserum, a linear peptide with an identical sequence as the antigen used for antibody production was synthesized onto a non-cleavable TentaGel-SH resin (Advanced ChemTech). The resin was deprotected, acetylated, and packed into disposable columns (Evergreen Scientific). Columns were equilibrated with Phosphate-buffered saline containing 0.05% Tween-20 (PBS-T) before being used for rabbit antiserum purification.

For purification, rabbit antiserum (1 mL) was first precleared by centrifugation (16,000 g), after which an equal volume of saturated ammonium sulfate was added. After one hour incubation at 4° C., precipitate was recovered by centrifugation and washed several times with 50% saturated ammonium sulfate. The precipitate was then dissolved in PBS-T and added to the affinity purification TentaGel column. The column was subsequently incubated overnight at 4° C., with end-over-end rotation, to allowing for binding to occur. The antibody-bound column was washed with PBS-T at room temperature until the wash eluent contained little or no protein (A280=0). Antibody fractions (1 mL) were eluted from column using 100 mM citric acid, pH 2.8, into tubes containing 250 μL of 1.5 M Tris and 150 mM NaCl, pH 8.0. The concentration of antibody in each fraction was determined using ultraviolet absorption spectroscopy and an IgG extinction coefficient ($\epsilon$280) of 1.35 (mg/mL)−1. The affinity purified antibody was stored at 4° C. and was generally stable for about 1 month.

Commercially available anti-transthyretin (anti-TTR) antibody produced in goat whole antiserum was purified using a previously established IgG purification method (Joustra and Lundgren 1969). In brief, 1 g of QAE Sephadex A-50 ion exchange resin was added to 50 mM ethylene diamine and 73 mM acetic acid, pH 7.0 and allowed to swell overnight at room temperature. After the initial swelling, the Sephadex media was transferred to a column and washed with the buffer in which it was initially swollen. 1 mL of goat antiserum was added to 1.25 mL of the wash buffer and added to the column—the minimum amount of resin bed in the column is ~3.2 mL per 2.25 mL of the diluted serum. The flow through was then collected and dialyzed extensively in phosphate-buffered saline (PBS). Flow through was found to contain pure IgG when polyacrylamide gel electrophoresis (PAGE) was performed in the presence of sodium dodecyl sulfate (SDS).

Protein Expression and Purification

A pET 21a (+) expression vector carrying TTR-(His)6 was transformed into Escherichia coli BL21-A1 competent cells (Invitrogen). Protein expression was induced with 1 mM isopropyl-β-D-thiogalactopyranoside when an absorbance (A600) of ~0.6 was reached. After 12-16 h incubation at 20° C., cells were harvested by centrifugation at 5000 g and purified using previously established methods with slight modifications19. Pelleted cells were resuspended in Buffer A (50 mM phosphate, 300 mM NaCl, 10 mM imidazole, and 20 mM β-mercaptoethanol, pH 8.0) and lysed by passage through an Emulsiflex-C5 (Avastin) for three cycles at 4° C. After centrifugation at 27,000 g for 30 min at 4° C., the supernatant was added to 5 mL of nickel-NTA agarose slurry (Qiagen), gently mixed for 1 h, and loaded onto a column. The column was washed several times with Buffer B (50 mM phosphate, 300 mM NaCl, 20 mM imidazole, and 20 mM β-mercaptoethanol, pH 8.0) and the fusion protein was eluted using Buffer C (50 mM phosphate, 300 mM NaCl, 250 mM imidazole, and 20 mM β-mercaptoethanol, pH 8.0). The protein solution was dialyzed extensively against 10 mM phosphate, aliquotted, and frozen at −20° C. for later use.

The purity of the protein solution was confirmed by size exclusion chromatography. TTR eluted as a single peak at ~11 mL, representing tetrameric TTR. Purity was also assessed by Coomassie-stained SDS-PAGE. Unboiled TTR samples produced two bands corresponding to dimeric and monomeric TTR, while boiled samples of TTR produced a single band corresponding to the monomeric form of the protein. Experiments were performed using recombinant TTR as well as wild-type TTR isolated from human plasma (Sigma Aldrich). The biophysical properties of both plasma and recombinant TTR were found to be identical.

TTR Fibril Formation Assay

A stock solution of TTR (5 mg/mL) was diluted with 50 mM sodium acetate, pH 4.5, to a final concentration of 0.2 mg/mL. Samples were then incubated at 37° C. for 72 hours. The extent of fibril formation was probed by turbidity measurements at 400 nm on a Jasco V-500 UV-visible spectrometer equipped with a temperature control unit. ThT was also used to assess the extent of fibril formation. In brief, a five-fold molar excess of ThT (Sigma) was added to each sample and left at room temperature for 30 minutes before measurements were taken. ThT fluorescence was monitored using a Photon Technology International C60 specrofluorimeter with the excitation and emission slit widths set to 4 nm. Spectra were obtained by scanning the fluorescence emission from 450 nm to 600 nm, with excitation at 442 nm.

Enzyme-Linked Immunosorbent Assay

For competition ELISA assays, TTR unfolded in the presence of 6 M GdnHCl[20] was used as bound antigen, while folded tetrameric TTR, monomeric TTR[11, 21] and TTR fibrils were used as competitors. In brief, a 96-well plate was coated with 100 ng of GdnHCl unfolded TTR per well and incubated overnight at room temperature. Each well was washed three times with PBS-T and subsequently blocked with PBS+1% bovine serum albumin (BSA) w/v (Sigma Aldrich) for two hours. Various concentrations of competitor (folded TTR, monomeric TTR, or TTR fibrils) in the presence of 1 µg/mL of affinity purified misTTR or a commercially available anti-TTR antibody (Sigma Aldrich) were added to wells and incubated for 1 h at room temperature. Wells were washed with PBS-T, and an HRP-conjugated anti-rabbit or anti-goat secondary antibody (1:5000) was added to wells and incubated at room temperature for 2 h. Wells were washed with PBST and 100 µL of the chromogenic substrate tetramethylbenzidine (Sigma Aldrich) was added. The reaction was stopped with 2 M H2SO4, and an absorbance reading (A450) of the ELISA plate was taken immediately using a plate reader (SpectraMax M5, Molecular Devices). All reported EC50 values were determined by fitting competition ELISA data to the following equation: y=(Amax-Amin)/(1+(x/EC50)ñ+Amin). $A_{max}$ and $A_{min}$ values were taken from the maximum absorbance value and minimum absorbance value of each competition ELISA curve, respectively.

Polyacrylamide Gel Electrophoresis in the Presence of Sodium Dodecyl Sulfate

Electrophoresis on polyacrylamide gels was performed in a buffered solution of 50 mM Tris-MES, pH 7.3, 0.2% SDS, and 1 mM EDTA. Home-made sample buffer consisting of 500 mM Tris (pH 7.3), 1 mM EDTA, 10% glycerol, 4% SDS, 0.075% Coomassie Brilliant Blue R-250, and 0.025% Phenol Red was used. Gels were run at a constant voltage of 120 V for 2 hours and stained overnight in a solution of 40% methanol, 10% acetic acid and 0.05% Coomassie Brilliant Blue R-250. Gels were then destained in a solution of 40% methanol and 10% acetic acid and subsequently imaged using a Bio-Rad Molecular Imager Gel Doc XR system (Bio-Rad Laboratories).

Dot Blot Assay

Nitrocellulose membrane (Pall Life Sciences) was presoaked in PBS, pH 7.4 for 5 min and transferred into a PBS solution containing 20% methanol. The membrane was subsequently air dried and 250 ng of each protein sample was spotted on. The blot was blocked overnight at 4° C. in 10% skim milk, washed several times with PBS-T, and incubated at room temperature with 1 µg/mL of affinity purified misTTR antibody for 2 h. After several washes, the blot was incubated with HRP-conjugated anti-rabbit secondary antibody (1:5000) for 1 h, and developed using an enhanced chemiluminescence substrate (Thermo Scientific).

Electron Microscopy

TTR samples were imaged using a Joel 1011 microscope operating at 80 kV. Samples were deposited on fresh continuous carbon films prepared from copper rhodium grids (Electron Microscopy Sciences). Grids were charged using a glow discharger for 15 seconds at 30 mA negative discharge before adding samples. Fibril solutions of 1 mg/mL were adsorbed to grids for 2 minutes before rinsing with 10 µL ddH20 for 10 seconds. Samples were then blotted using No. 2 Whatman Filter paper and stained with freshly filtered 2% uranyl acetate for 15 seconds.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Dunker, A. K., Lawson, J. D., Brown, C. J., Williams, R. M., Romero, P., Oh, J. S., Oldfield, C. J., Campen, A. M., Ratliff, C. M., Hipps, K. W., Ausio, J., Nissen, M. S., Reeves, R., Kang, C., Kissinger, C. R., Bailey, R. W., Griswold, M. D., Chiu, W., Garner, E. C. and Obradovic, Z. (2001). Intrinsically disordered protein. *J Mol Graph Model* 19, 26-59.
2. Come, J. H., Fraser, P. E. and Lansbury, P. T., Jr. (1993). A kinetic model for amyloid formation in the prion diseases: importance of seeding. *Proc Natl Acad Sci USA* 90, 5959-63.
3. Bieschke, J., Herbst, M., Wiglenda, T., Friedrich, R. P., Boeddrich, A., Schiele, F., Kleckers, D., Lopez del Amo, J. M., Gruning, B. A., Wang, Q., Schmidt, M. R., Lurz, R., Anwyl, R., Schnoegl, S., Fandrich, M., Frank, R. F., Reif, B., Gunther, S., Walsh, D. M. and Wanker, E. E. (2012). Small-molecule conversion of toxic oligomers to nontoxic beta-sheet-rich amyloid fibrils. *Nat Chem Biol* 8, 93-101.
4. Sacchettini, J. C. and Kelly, J. W. (2002). Therapeutic strategies for human amyloid diseases. *Nat Rev Drug Discov* 1, 267-75.

5. Rakhit, R., Robertson, J., Vande Velde, C., Horne, P., Ruth, D. M., Griffin, J., Cleveland, D. W., Cashman, N. R. and Chakrabartty, A. (2007). An immunological epitope selective for pathological monomer-misfolded SOD1 in ALS. *Nat Med* 13, 754-9.
6. Paramithiotis, E., Pinard, M., Lawton, T., LaBoissiere, S., Leathers, V. L., Zou, W. Q., Estey, L. A., Lamontagne, J., Lehto, M. T., Kondejewski, L. H., Francoeur, G. P., Papadopoulos, M., Haghighat, A., Spatz, S. J., Head, M., Will, R., Ironside, J., O'Rourke, K., Tonelli, Q., Ledebur, H. C., Chakrabartty, A. and Cashman, N. R. (2003). A prion protein epitope selective for the pathologically misfolded conformation. *Nat Med* 9, 893-9.
7. Kayed, R., Head, E., Thompson, J. L., McIntire, T. M., Milton, S. C., Cotman, C. W. and Glabe, C. G. (2003). Common structure of soluble amyloid oligomers implies common mechanism of pathogenesis. *Science* 300, 486-9.
8. Palha, J. A., Moreira, P., Olofsson, A., Lundgren, E. and Saraiva, M. J. (2001). Antibody recognition of amyloidogenic transthyretin variants in serum of patients with familial amyloidotic polyneuropathy. *J Mol Med (Berl)* 78, 703-7.
9. Goldsteins, G., Persson, H., Andersson, K., Olofsson, A., Dacklin, I., Edvinsson, A., Saraiva, M. J. and Lundgren, E. (1999). Exposure of cryptic epitopes on transthyretin only in amyloid and in amyloidogenic mutants. *Proc Natl Acad Sci USA* 96, 3108-13.
10. Bergstrom, J., Engstrom, U., Yamashita, T., Ando, Y. and Westermark, P. (2006). Surface exposed epitopes and structural heterogeneity of in vivo formed transthyretin amyloid fibrils. *Biochem Biophys Res Commun* 348, 532-9.
11. Lai, Z., Colon, W. and Kelly, J. W. (1996). The acid-mediated denaturation pathway of transthyretin yields a conformational intermediate that can selfassemble into amyloid. *Biochemistry* 35, 6470-82.
12. Liu, K., Cho, H. S., Lashuel, H. A., Kelly, J. W. and Wemmer, D. E. (2000). A glimpse of a possible amyloidogenic intermediate of transthyretin. *Nature Structural Biology* 7, 754-7.
13. Colon, W. and Kelly, J. W. (1992). Partial Denaturation of Transthyretin Is Sufficient for Amyloid Fibril Formation Invitro. *Biochemistry* 31, 8654-8660.
14. Kelly, J. W. (1996). Alternative conformations of amyloidogenic proteins govern their behavior. *Curr Opin Struct Biol* 6, 11-7.
15. Kelly, J. W. (1997). Amyloid fibril formation and protein misassembly: a structural quest for insights into amyloid and prion diseases. *Structure* 5, 595-600.
16. Arslan, P. E., Mulligan, V. K., Ho, S. and Chakrabartty, A. (2010). Conversion of Abeta42 into a folded soluble native-like protein using a semi-random library of amphipathic helices. *J Mol Bio!* 396, 1284-94.
17. Walsh, P., Simonetti, K. and Sharpe, S. (2009). Core structure of amyloid fibrils formed by residues 106-126 of the human prion protein. *Structure* 17, 417-26.
18. Jiang, X., Buxbaum, J. N. and Kelly, J. W. (2001). The V122I cardiomyopathy variant of transthyretin increases the velocity of rate-limiting tetramer dissociation, resulting in accelerated amyloidosis. *Proc Natl Acad Sci USA* 98, 14943-8.
19. Matsubara, K., Mizuguchi, M. and Kawano, K. (2003). Expression of a synthetic gene encoding human transthyretin in Escherichia coli. *Protein Expr Purif* 30, 55-61.
20. Lai, Z., McCulloch, J., Lashuel, H. A. and Kelly, J. W. (1997). Guanidine hydrochloride-induced denaturation and refolding of transthyretin exhibits a marked hysteresis: equilibria with high kinetic barriers. *Biochemistry* 36, 10230-9.
21. Lashuel, H. A., Lai, Z. and Kelly, J. W. (1998). Characterization of the transthyretin acid denaturation pathways by analytical ultracentrifugation: implications for wild-type, V30M, and L55P amyloid fibril formation. *Biochemistry* 37, 17851-64.

The invention claimed is:

1. A method for preparing an antibody or binding fragment thereof that specifically binds EHAEVVFTA (SEQ ID NO:1) and selectively binds misfolded transthyretin (TTR) relative to natively folded TTR, the method comprising immunizing a non-human subject with an immunogen comprising a peptide consisting of the sequence EHAEVVFTA (SEQ ID NO:1) and isolating the antibody or binding fragment thereof, wherein the antibody binds TTR amyloid fibrils found in situ in a biological sample.

2. The method of claim 1, wherein the immunogen comprises a multiple antigenic peptide (MAP) dendrimer comprising a plurality of branches wherein each branch comprises the peptide consisting of the sequence EHAEVVFTA (SEQ ID NO:1).

3. The method of claim 1, wherein the immunogen further comprises an immunogenicity enhancing molecule or solubility enhancing molecule.

4. The method of claim 3, wherein the immunogenicity enhancing molecule is keyhole limpet hemocyanin (KLH) or albumin.

5. The method of claim 1, wherein the immunogen is comprised in a composition, the composition further comprising an adjuvant.

6. The method of claim 1, further comprising forming a monoclonal antibody-producing hybridoma.

7. The method of claim 6, wherein forming the monoclonal antibody-producing hybridoma comprises isolating an antibody producing cell from the non-human subject and fusing said cell with a myeloma cell, forming the monoclonal antibody-producing hybridoma.

8. The method of claim 6, further comprising isolating the monoclonal antibody from the monoclonal antibody-producing hybridoma.

9. The method of claim 1, wherein the method further comprises humanizing the isolated antibody or binding fragment to produce a humanized antibody or binding fragment thereof.

10. The method of claim 9, wherein the humanized antibody or binding fragment thereof is generated by humanizing surface residues of the antibody or binding fragment thereof produced by the non-human animal.

11. The method of claim 1, wherein the method further comprises fragmenting the antibody to produce a Fab, Fab' or F(ab')₂ binding fragment.

12. The method of claim 1, further comprising purifying the antibody or binding fragment thereof.

13. The method of claim 12, wherein the purifying comprises affinity purifying the antibody or binding fragment thereof.

14. The method of claim 1, wherein the non-human subject is a rabbit or a rodent.

15. The method of claim 1, wherein said isolating said antibody or binding fragment thereof comprises determining antibody or binding fragment selectively binds misfolded TTR relative to natively folded TTR and isolating said antibody or binding fragment thereof.

16. The method of claim 15, wherein the binding selectivity is at least two fold more for misfolded TTR compared to natively folded TTR.

17. A method for preparing an antibody or binding fragment thereof that selectively binds misfolded transthyretin (TTR) relative to natively folded TTR, the method comprising immunizing a non-human subject with an immunogen comprising a peptide consisting of EHAEVVFTA (SEQ ID NO:1) and isolating said antibody or binding fragment thereof, wherein the antibody binds TTR amyloid fibrils found in situ in a biological sample.

18. The method of claim 17, wherein said isolating said antibody or binding fragment thereof comprises determining antibody or binding fragment thereof that selectively binds misfolded TTR relative to natively folded TTR and isolating said antibody or binding fragment thereof.

19. The method of claim 17, wherein the method further comprises humanizing the isolated antibody or binding fragment to produce a humanized antibody or binding fragment thereof.

20. The method of claim 17, wherein the humanized antibody or binding fragment thereof is generated by humanizing surface residues of the antibody or binding fragment thereof produced by the non-human animal.

* * * * *